US012203923B2

(12) United States Patent
Lim et al.

(10) Patent No.: US 12,203,923 B2
(45) Date of Patent: Jan. 21, 2025

(54) BIOSENSOR CARTRIDGES AND TEST DEVICE THEREFOR

(71) Applicant: LG ELECTRONICS INC., Seoul (KR)

(72) Inventors: Kyoungtaek Lim, Seoul (KR); Taekyu Choi, Seoul (KR); Younghwan Kim, Seoul (KR); Seonggeun Kim, Seoul (KR); Changseok Kim, Seoul (KR); Kyungho Kong, Seoul (KR); Kyounghwa Kim, Seoul (KR); Youngrae Lee, Seoul (KR); Inkwan Yeo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 156 days.

(21) Appl. No.: 17/993,841

(22) Filed: Nov. 23, 2022

(65) Prior Publication Data

US 2023/0333085 A1    Oct. 19, 2023

(30) Foreign Application Priority Data

Apr. 19, 2022    (KR) .................. 10-2022-0047913

(51) Int. Cl.
*G01N 33/487*    (2006.01)
*A61B 5/00*    (2006.01)
(Continued)

(52) U.S. Cl.
CPC ..... *G01N 33/48785* (2013.01); *A61B 5/0022* (2013.01); *A61B 5/05* (2013.01);
(Continued)

(58) Field of Classification Search
USPC ................................................ 324/149, 73.1
See application file for complete search history.

(56) References Cited

U.S. PATENT DOCUMENTS 9,805,165 B2    10/2017    Xiang et al.
2004/0244151 A1*    12/2004    Sakata ............. G01N 33/48771
                                                                23/306
(Continued)

FOREIGN PATENT DOCUMENTS

JP    2000-258493 A    9/2000
JP    2003-149192 A    5/2003
(Continued)

OTHER PUBLICATIONS

Attached is the International Search Report for International Application No. PCT/KR2023/001417, dated May 15, 2023.
(Continued)

*Primary Examiner* — Incent Q Nguyen
(74) *Attorney, Agent, or Firm* — Birch, Stewart, Kolasch & Birch, LLP

(57) ABSTRACT

Provided is a probe device for testing a sensor chip that detects a target material from an analysis specimen, has a reactant reacting specifically with the target material, and transmits a generated electrical signal through a pad. The probe device can include a lower housing accommodating a circuit board electrically connectable to an external test device; a middle housing positioned on the lower housing, coupled to the lower housing, and having the sensor chip mounted thereon; a probe module having probe pins for connecting a pad of the sensor chip and a connection pad of the circuit board to each other; and an upper housing positioned on the middle housing, coupled to the middle housing, having a recessed portion that opens the sensor chip, and having a guide area for aligning the probe module on the pads of the sensor chip and the circuit board.

20 Claims, 23 Drawing Sheets

(51) Int. Cl.
    *A61B 5/05*         (2021.01)
    *A61B 10/00*       (2006.01)
    *B01L 3/00*         (2006.01)
    *G01N 27/414*      (2006.01)
    *G01N 33/543*      (2006.01)
    *G06K 7/14*         (2006.01)
    *G06Q 20/32*       (2012.01)
    *H01R 12/72*       (2011.01)
    *H05K 1/18*         (2006.01)

(52) U.S. Cl.
    CPC ............ *A61B 5/742* (2013.01); *A61B 5/7495* (2013.01); *A61B 10/0045* (2013.01); *B01L 3/502715* (2013.01); *G01N 27/4145* (2013.01); *G01N 33/48707* (2013.01); *G01N 33/48778* (2013.01); *G01N 33/5438* (2013.01); *G06K 7/1417* (2013.01); *G06K 7/1447* (2013.01); *G06Q 20/3223* (2013.01); *H01R 12/72* (2013.01); *H05K 1/181* (2013.01); *B01L 2200/027* (2013.01); *B01L 2200/04* (2013.01); *B01L 2200/16* (2013.01); *B01L 2300/022* (2013.01); *B01L 2300/023* (2013.01); *B01L 2300/027* (2013.01); *B01L 2300/0636* (2013.01); *B01L 2300/0645* (2013.01); *B01L 2300/0663* (2013.01); *B01L 2300/0848* (2013.01); *B01L 2300/0861* (2013.01); *H01R 2201/12* (2013.01); *H01R 2201/20* (2013.01); *H05K 2201/10151* (2013.01); *H05K 2201/10166* (2013.01); *H05K 2201/10265* (2013.01); *H05K 2201/10386* (2013.01)

(56) References Cited

U.S. PATENT DOCUMENTS

2009/0124876 A1* 5/2009 Nakamura ......... A61B 5/15194
                                                          600/576
2015/0268186 A1   9/2015 Pagels 2016/0084793 A1* 3/2016 Chen .................. G01N 27/3274
                                                         205/782
2019/0041355 A1   2/2019 Merriman et al.
2021/0129133 A1   5/2021 Ohta et al.

FOREIGN PATENT DOCUMENTS

| | | |
|---|---|---|
| JP | 2008-46094 A | 2/2008 |
| JP | 2013-83506 A | 5/2013 |
| JP | 2020-126077 A | 8/2020 |
| KR | 20-0311804 Y1 | 5/2003 |
| KR | 10-2008-0110356 A | 12/2008 |
| KR | 10-2010-0072533 A | 7/2010 |
| KR | 10-2010-0103932 A | 9/2010 |
| KR | 10-2011-0064754 A | 6/2011 |
| KR | 10-2013-0012744 A | 2/2013 |
| KR | 10-1323373 B1 | 10/2013 |
| KR | 10-2014-0120138 A | 10/2014 |
| KR | 10-1507317 B1 | 3/2015 |
| KR | 10-2016-0017684 A | 2/2016 |
| KR | 10-1591379 B1 | 2/2016 |
| KR | 10-2016-0065562 A | 6/2016 |
| KR | 10-2017-0007582 A | 1/2017 |
| KR | 10-1779705 B1 | 9/2017 |
| KR | 10-2030272 B1 | 10/2019 |
| KR | 10-2019-0136580 A | 12/2019 |
| KR | 10-2021-0076854 A | 6/2021 |
| KR | 10-2021-0151487 A | 12/2021 |
| WO | WO 2019/208901 A1 | 10/2019 |
| WO | WO 2021/013392 A1 | 1/2021 |
| WO | WO 2021/224907 A1 | 11/2021 |

OTHER PUBLICATIONS

Also attached is the International Search Report for International Application No. PCT/KR2023/001423, dated May 24, 2023.
Also attached is the International Search Report for International Application No. PCT/KR2023/002760, dated Jun. 20, 2023.
Also attached is the International Search Report for International Application No. PCT/KR2023/002762, dated Jun. 20, 2023.
Also attached is the International Search Report for International Application No. PCT/KR2023/002765, dated Jun. 20, 2023.

* cited by examiner

BIOSENSOR CARTRIDGES AND TEST DEVICE THEREFOR

CROSS-REFERENCE TO RELATED APPLICATIONS

This application claims priority to the Korean Patent Application No. 10-2022-0047913 filed in the Republic of Korea on Apr. 19, 2022, which is hereby incorporated by reference in its entirety into the present application.

BACKGROUND

Field

The present disclosure relates to a biosensor cartridge including a biosensor and a test device for testing the biosensor chip.

Discussion of the Related Art

Recently, as diseases having a high infectivity spread, a need for rapid diagnosis and self-diagnosis of the disease in medical fields such as homes, hospitals, and public health centers, is increasing.

Therefore, it is required to develop an immunoassay platform that does not require specialized knowledge or complicated procedures and has a short analysis time.

A biosensor generates an electrical, optical signal, and a color that changes according to a selective reaction between probe material having reactivity for a specific target material contained in a body fluid such as sweat and saliva, or in biological substances such as blood or urine, and the target material. Accordingly, the presence of a specific target material can be checked by using the biosensor.

Conventionally, a strip-type rapid kit has been widely used, and simple color development (e.g., the test, such as a dipstick, will change colors if the results are positive) is performed by determining whether a bio-target material having a certain concentration or higher is present.

However, in the case of labeling the target material by color development, the conversion of color development can be inaccurate depending on the concentration of the target material, and the color development must be visually determined. Therefore, the accuracy is different depending on a user who views the test results.

To compensate for this inaccuracy, a biosensor that generates an electrical signal, as opposed to a color development, has been proposed.

In a biosensor that generates an electrical signal, a target material is coupled to a small thin film semiconductor structure, an electrical conductivity of the semiconductor structure is changed by the target material, and the target material is detected through a change in electrical conductivity. In particular, when a target material is combined (e.g., disposed) in a channel, if an electrochemical reaction occurs or the target material itself has a charge, electrons or holes in the semiconductor structure are accumulated or depleted due to the electric field effect caused by the combination of the probe material and the target material. Thus, the electrical conductivity is changed, which is read as a change in the amount of current. In such an electrochemical-based biosensor, the resistance of an electrode itself and the interfacial property of a channel where the electrochemical reaction occurs are very important.

Meanwhile, the biosensor including a channel of a semiconductor structure, an electrode for measuring an electrical signal has a very thin thickness as it is also manufactured in a dicing unit (e.g., a process where a sheet of electrodes is diced or cut into individual electrodes, which may be performed using a laser, for instance). Thus, short circuit or contamination frequently can occur due to damage to the electrode or damage to the channel during a process of coupling with a measuring device for measuring an amount of current.

In order to prevent this possibility of a short circuit, an existing biosensor is provided as a structure including a sensor portion for sensing a target material, and a connection portion for connecting the sensor portion and measurement equipment.

That is, an electrode of the existing biosensor can be configured with a connection portion that is extended from the sensor portion for sensing the target material, extended from an end of the board, and connected to the measuring equipment.

However, even if such an electrode is formed by being extended, since the electrode is formed in a dicing step, the size of the sensor chip itself increases. This can cause a limitation in that a semiconductor wafer becomes unnecessarily large, thereby reducing a chip yield.

Efforts to miniaturize the sensor chip are continuously needed. In particular, a method of minimizing formation of other connection portions and pad portions while maintaining a constant contact area with a specimen is needed.

However, the miniaturization of the sensor chip needs miniaturization of test equipment.

In previous test equipment, a processing device for processing test data and a probe terminal for performing a test are connected to each other by wire or wireless, and the probe terminal is manually brought into contact with a test position on the corresponding chip or a chip is loaded to a specific position to automatically perform the test.

Since the processing device of the test equipment and the probe terminal are very large compared to the sensor chip, which is a testing body, it is difficult to perform a test meticulously.

In addition, in the case of the sensor chip, since a pad is formed on one side (e.g., a first side) and an area other than a reaction area is minimized, and thus, in the case of test equipment that reads a signal from the pad disposed in the minimized area and performs a test, it may be not possible for several probe terminals to be connected to pads at the same time (e.g., simultaneously).

In order to address such a problem, a technique for performing a performance test of a chip by applying a probe socket is disclosed.

In the case of Korean Patent Application Publication No. 10-2017-007582, a vacuum socket is disclosed as the medium.

The vacuum socket is applied to a semiconductor chip, and a technology in which a semiconductor chip is mounted inside, a separate printed circuit board having a plurality of pads matching the semiconductor is mounted therebelow, and the two elements are flip-chip bonded and connected to each other through a probe is provided.

However, in the case of Korean Patent Application Publication No. 10-2017-007582, physical bonding is attempted by flip-chip bonding of a semiconductor chip and a printed circuit board for a test, and the semiconductor chip to be bonded should be disposed together with the printed circuit board after the test is completed.

In addition, since the semiconductor chip disposed outside is eventually tested at a test site using external test equipment, it is important that the vacuum socket operates as a means for moving the semiconductor chip.

RELATED DOCUMENT

Korean Patent Application Publication No. 10-2017-007582 (published on Jan. 19, 2017).

SUMMARY OF THE DISCLOSURE

The disclosure has been made in view of the above limitations, and can provide a biosensor cartridge including a sensor chip and provide a separate probe device for testing performance of the sensor chip.

The disclosure can further provide a probe device capable of testing the sensor chip with the circuit board itself without requiring a separate circuit board by directly applying the circuit board and the sensor chip applied to the biosensor cartridge.

The disclosure can further provide a probe device that is easily deformable when a configuration of a pad changes as a configuration for electrical connection is implemented in a po-go pin shape.

In accordance with an aspect of the present disclosure, there is provided a probe device for testing a sensor chip that detects a target material from an applied analysis specimen, has a reactant reacting specifically with the target material, and transmits a generated electrical signal through a pad. The probe device includes: a lower housing accommodating a circuit board comprising a connection terminal configured to be electrically connected to an external test device; a middle housing positioned on the lower housing, coupled to the lower housing, and having the sensor chip mounted thereon; a probe module having probe pins for connecting a pad of the sensor chip and a connection pad of the circuit board to each other; and an upper housing positioned on the middle housing, coupled to the middle housing, having a recessed portion that opens the sensor chip, and having a guide area for aligning the probe module on the pad of the sensor chip and the pad of the circuit board.

The middle housing can include a guide hole which exposes each pad of the circuit board and through which the probe pin passes.

The middle housing can include a chip area that defines a position of the sensor chip so that the pad of the sensor chip and the guide hole are disposed adjacent to each other.

The probe pin module can include: a support part for simultaneously supporting a plurality of probe pins; and a plurality of probe pins passing through the support part and respectively contacting the pad of the sensor chip and the pad of the circuit board.

A length of the probe pin can be adjustable according to heights of the sensor chip and the circuit board.

The support part can comprises a plurality of through-holes passing through the plurality of probe pins, respectively, and the plurality of probe pins are insulated from each other by the support part.

One ends of the probe pins can be exposed above the support part, the other ends thereof can be exposed below the support part, and when connection is required between the pad of the sensor chip and the connection pad of the circuit board, the connection can be electrically made at the other ends of the probe pins.

The upper housing can have an inclination so that the recessed portion accommodates an electrolyte fluid.

The guide area of the upper housing can further include a probe pin guide for having the support part of the probe pin module seated and supported.

The probe pin guide can be formed to protrude from a body portion of the upper housing by a predetermined height.

The probe device can further include a cover guide disposed on the probe pin guide and housing one ends of the probe pins.

The lower housing can include a body portion defining an area of the probe device, and at least one coupling protrusion protruding from an upper surface of the body portion.

The at least one coupling protrusion can simultaneously pass through the middle housing and the upper housing and be coupled thereto.

The lower housing and the middle housing can include coupling holes coupled to peripheral areas by a coupling member.

The probe device can include a coupling hook coupled to a side surface of the upper housing so as to be pivotally rotated, and engaged with a rear surface of the lower housing or the middle housing.

A reference resistance of the sensor chip can be measured by inserting a connection terminal of the circuit board into a test device with an electrolyte fluid applied to the receiving portion.

When a biosensor cartridge including a sensor chip is provided, a probe device with a simplified structure is provided to test performance of a sensor chip diced from one semiconductor wafer, thereby enabling the test without a large-sized prober.

In addition, since performance of a sensor chip is tested by directly applying a circuit board and a sensor chip which are applied to a biosensor cartridge, an additional circuit board for testing is not needed, thereby reducing cost and time.

In addition, a configuration for electrical connection between a circuit board and a sensor chip in a probe device is implemented in a po-go pin shape, and thus, when the configuration of the sensor chip and the pad of the circuit board changes, it is possible to respond to the change by changing the shape of the po-go pin, without deformation of an entire housing.

BRIEF DESCRIPTION OF THE DRAWINGS

The above and other objects, features and advantages of the present disclosure will be more apparent from the following detailed description in conjunction with the accompanying drawings, in which.

DETAILED DESCRIPTION OF THE EMBODIMENTS

Figure 1:
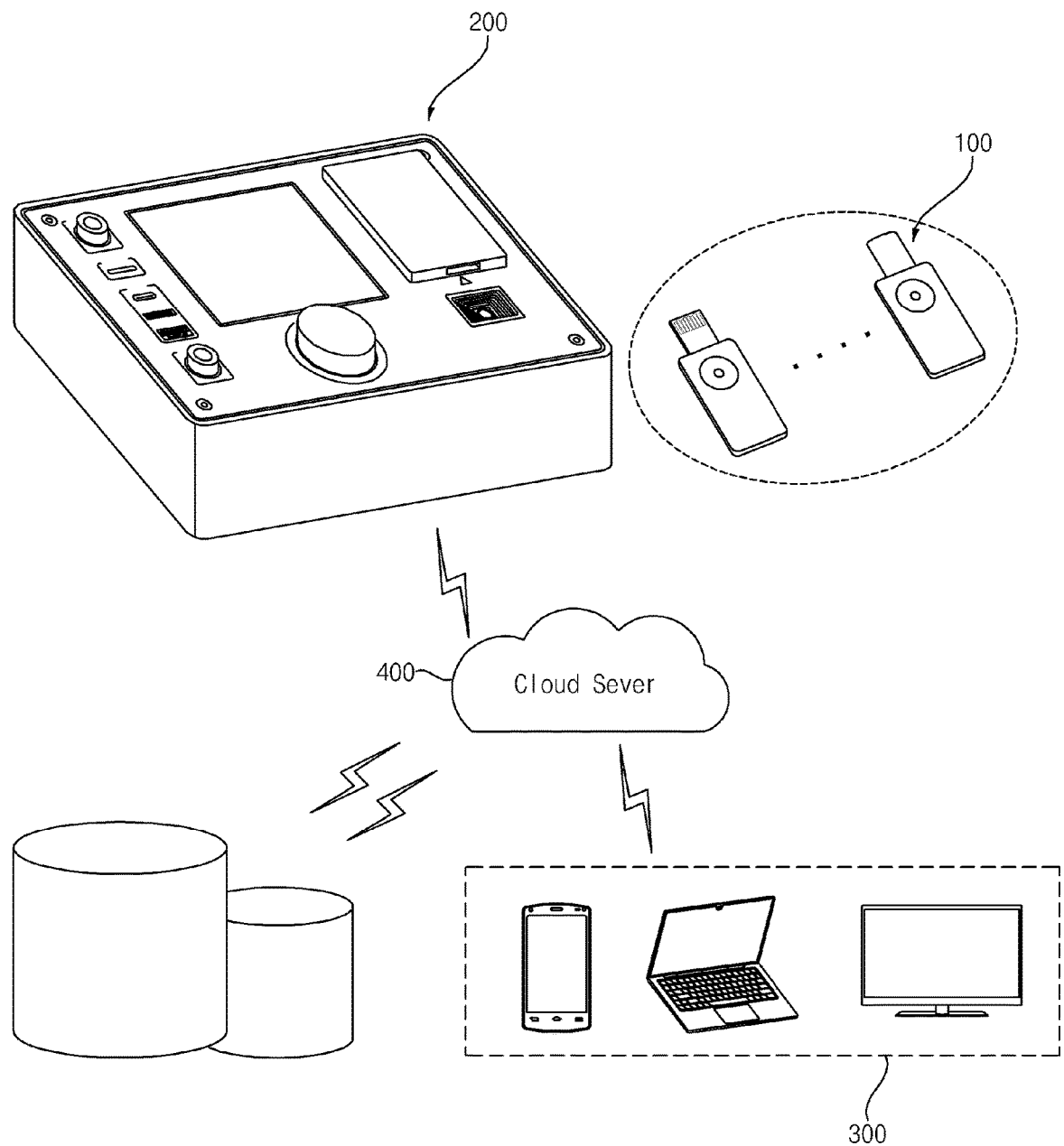
FIG. 1 is a diagram illustrating a biosensor system according to one or more embodiments of the disclosure.

Expressions referring to directions such as "front(F)/rear (R)/left (Le)/right (Ri)/up (U)/down (D)" mentioned below are defined as shown in the drawings, but, this is for the purpose of explaining an embodiment so that it can be clearly understood, and it is obvious that each direction can be defined differently depending on where standard is set.

The use of terms such as 'first, second', etc. added before the components mentioned below is only to avoid confusion of the referred components, and is irrelevant to the order, importance, or master-slave relationship between the components. For example, an embodiment including only a second component without a first component can also be implemented.

In the drawings, the thickness or size of each component is exaggerated, omitted, or schematically illustrated for convenience and clarity of description. In addition, the size and area of each component do not fully reflect the actual size or area.

In addition, angles and directions mentioned in the process of explaining a structure of the present embodiment are based on those described in the drawings. In the description of the structure in the specification, if a reference point for the angle and a positional relationship are not clearly mentioned, the related drawings can be referred to.

In the present specification, target materials are biomaterials representing a specific substrate, and are interpreted as having the same meaning as analytical bodies or analytes. In the present embodiment, the target material can be an antigen. In the present specification, probe material is a biomaterial that specifically binds to a target material, and is interpreted as having the same meaning as a receptor or an acceptor. In the present embodiment, the probe material can be an antibody.

The electrochemical-based biosensor combines the analytical ability of the electrochemical method with a specificity of biological recognition, and detects a biological recognition phenomenon for a target material as a change in current or potential, by immobilizing or containing a material having biological specificity, i.e., probe material such as an enzyme, an antigen, an antibody, or a biochemical material, on the surface of an electrode.

Hereinafter, a biosensor system according to the present embodiment will be described with reference to FIGS. 1 and 2.

Figure 2:
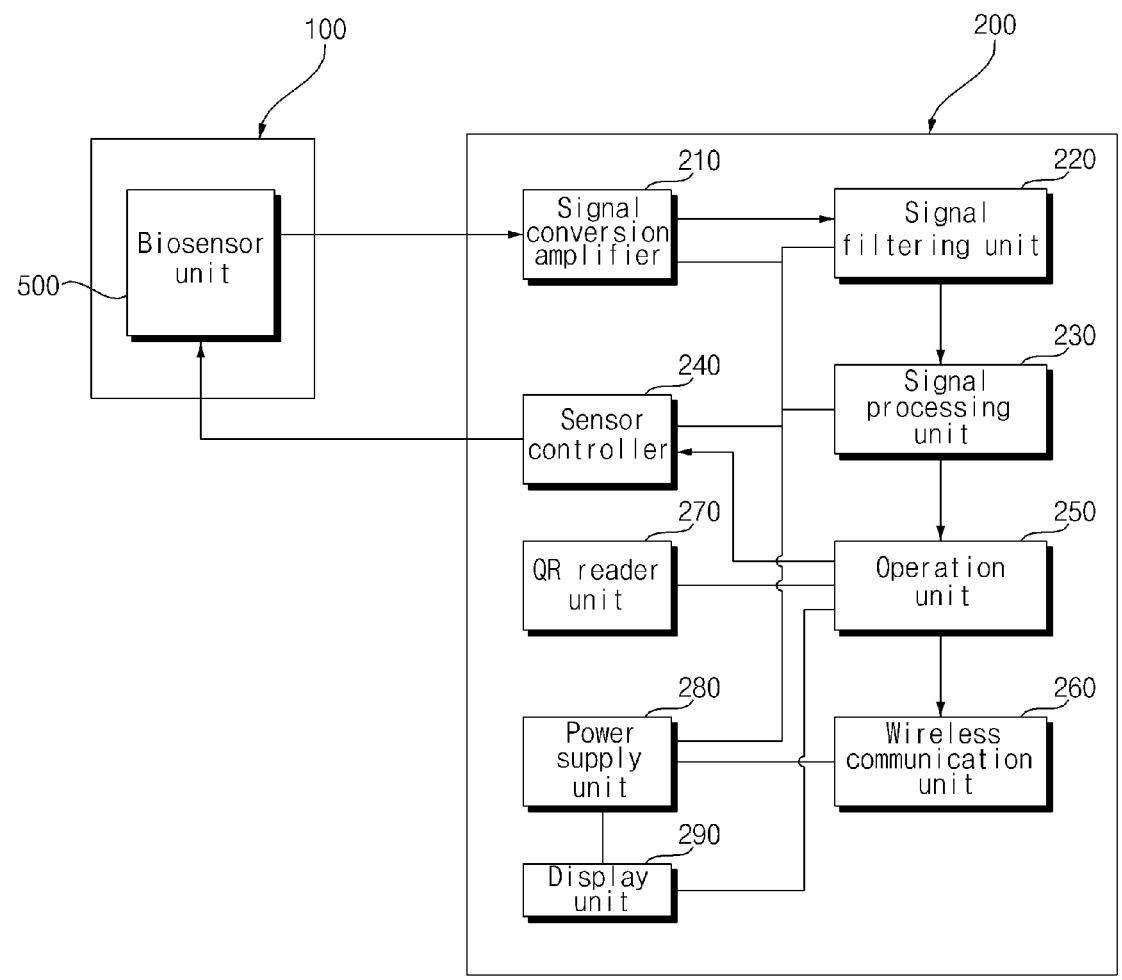
FIG. 2 is a configuration diagram of a biosensor diagnostic device and a biosensor cartridge of FIG. 1.

FIG. 1 is a diagram illustrating a biosensor system according to the present embodiment, and FIG. 2 is a configuration diagram of a biosensor diagnostic device 200 and a biosensor cartridge 100 of FIG. 1.

Hereinafter, a biosensor system according to the present embodiment will be described with reference to FIGS. 1 and 2.

FIG. 1 is a diagram illustrating a biosensor system according to the present embodiment, and FIG. 2 is a configuration diagram of a biosensor diagnostic device 200 and a biosensor cartridge 100 of FIG. 1.

Referring to FIG. 1, the biosensor system according to the present embodiment includes a biosensor diagnostic device 200, a plurality of biosensor cartridges 100 (e.g., at least one biosensor cartridge 100), and at least one server 400.

When the plurality of biosensor cartridges 100 are inserted (e.g., the plurality of biosensor cartridges 100 can be inserted into the biosensor diagnostic device 200 simultaneously), the biosensor diagnostic device 200 reads a detection signal from the biosensor cartridges 100 to read the presence of a target material for each biosensor cartridge 100.

The biosensor diagnostic device 200 is a portable integrated diagnostic device 200 that detects a current change for the presence of a trace amount of a target material from the biosensor cartridge 100, and accordingly diagnoses a disease and delivers the diagnosis result to a user.

To this end, the biosensor diagnostic device 200 can be provided to be portable by integrating each functional block, miniaturizing it, and integrating it in one case.

The biosensor diagnostic device 200 can be moved regardless of location, regardless of the presence or absence of an external power source by mounting a battery 281 therein. In addition, the diagnostic device 200 includes a function of compensating a reproducibility and non-uniformity of a sensor by including a pre-processing process of correcting a detection signal from the biosensor cartridge 100 so as to be able to read a minute signal change.

In addition, the biosensor diagnostic device 200 includes a QR reader that reads a QR code disposed on the rear surface of the biosensor cartridge 100 and receives environmental information for genuine product certification of the biosensor cartridge 100 to perform genuine product certification and a communication module that can transmit and receive signals for genuine product certification with an external cloud server 400.

In the biosensor diagnostic device 200, a program algorithm or application for diagnosing a disease by measuring and analyzing the detection signal from the biosensor cartridge 100 can be installed, and different algorithms are executable according to the type of each biosensor cartridge 100. That is, each type of biosensor cartridge 100 will require a different algorithm or application, the different algorithms/applications are stored a memory of the biosensor diagnostic device 200.

In addition, the biosensor diagnostic device 200 includes a display unit 290 for directly displaying the diagnosis result to a user, and is designed to be directly manipulated through a user interface 296, 297, 294.

The detailed configuration of the integrated biosensor diagnostic device 200 will be described later.

Meanwhile, the biosensor system includes a plurality of biosensor cartridges 100 which is inserted into the biosensor diagnostic device 200 to provide detection signals.

Each of the biosensor cartridges 100 is electrically connected to a diagnostic device 200 in which an algorithm capable of measuring and analyzing an electrical detection signal generated in a biosensor chip 500 is installed.

Specifically, as shown in FIG. 1, the biosensor cartridge 100 can be inserted into and electrically connected to a cartridge insertion module 2911 of the integrated biosensor diagnostic device 200.

The biosensor cartridge 100 can accommodate the sensor chip 500 corresponding to a biosensor unit 500 (e.g., the sensor chip 500 can be designated a biosensor unit 500) in a housing 110, 120, and the housing 110, 120 can accommodate a circuit board 150 including a circuit pattern that extends to a connection terminal 153 that is connected to an electrode pad of the sensor chip 500 and inserted into the insertion module 2911 of an external biosensor diagnostic device 200.

The housing 110, 120 can be separated into an upper housing 110 and a lower housing 120, and the upper housing 110 and the lower housing 120 are coupled and fixed to each other while accommodating the sensor chip 500 and the circuit board, thereby constituting a single biosensor cartridge 100.

The biosensor cartridge 100 has a connection terminal 153 for physical and electrical coupling with the biosensor diagnostic device 200 exposed from one end to the outside, and a solution accommodating portion 119 for accommodating a specimen (e.g., analysis specimen) is formed on the surface (e.g., an upper surface) of the upper housing 110.

The solution accommodating portion 119 exposes a part of the inner sensor chip 500, and when a specimen is accommodated in the solution accommodating portion 119, the charge concentration of a channel of the sensor chip 500 is varied according to the antigen-antibody reaction of the sensor chip 500, so that the current flowing through the electrode of the sensor chip 500 varies. The varied current is read by the diagnostic device 200 through the connection terminal 153.

In this case, in order to secure the charge mobility of the sensor chip 500, a channel can be implemented with various materials, and in particular, a channel can be implemented by using graphene. However, alternate materials can be used for the channel of the sensor chip 500, such as silicon, silicon carbide, germanium, aluminum nitride, indium, gallium nitride and gallium arsenide.

The detailed configuration of the biosensor cartridge 100 will be described in detail later.

Meanwhile, the biosensor system can include at least one server 400.

The server 400 can be a manufacturer server 400, and the manufacturer server 400 can include a processor capable of processing a program. The function of the server 400 can be performed by the manufacturer's central computer (e.g., a cloud computer).

For example, the server 400 can be a server 400 operated by a manufacturer of the biosensor cartridge 100 and the diagnostic device 200. As another example, the server 400 can be a server 400 that is provided in a building, and stores state information on devices in the building or stores content required by home appliances in the building.

The server 400 can store firmware information and diagnostic information on the diagnostic device 200, and transmit certification information on the biosensor cartridge 100 requested from the diagnostic device 200.

The server 400 in a biosensor system can be one of a plurality of cloud servers 400 of a manufacturer, and can be provided within the biosensor system while a plurality of cloud servers 400 are simultaneously included to allow access to one biosensor diagnostic device 200.

As described above, when a plurality of cloud servers 400 can simultaneously access one biosensor diagnostic device 200, the biosensor diagnostic device 200 can match the ranks with respect to the plurality of cloud servers 400, and can send an certification request sequentially from the highest priority. In this case, if a response signal is not received from the priority server 400, an certification request can be sent to the server 400 of the next priority.

The server 400 can authenticate the biosensor cartridge 100 and provide the certification result to the biosensor diagnostic device 200.

In addition, the server 400 can provide calibration data and update data for the product of a corresponding ID, and can transmit to the communicating biosensor diagnostic device 200.

The server 400 can also generate and distribute an upgraded version of a program for analysis for each biosensor cartridge 100.

To this end, the server 400 can receive history information on the manufacturing date, manufacturing conditions, sensor type, test result, etc. of the biosensor cartridge 100 of a manufacturer from a manufacturing server of a separate manufacturer.

In addition, the server 400 can periodically generate and distribute an upgraded version of a program provided to each diagnostic device 200 by receiving, accumulating, and machine learning the diagnostic result values for a corresponding product.

Meanwhile, the biosensor system of the present embodiment can further include a plurality of user terminals 300, but is not limited thereto. User terminals can include mobile terminals, laptops, touchpads, and the like.

When the user terminal 300 is included in the system, the biosensor diagnostic device 200 or the cloud server 400 can transmit data on the diagnosis result to the communicating user terminal 300.

To this end, a dedicated application for the user terminal 300 can be provided from the manufacturer server 400, and various processing of diagnostic data is possible by storing and executing the application in the user terminal 300.

For example, when a user is infected with the same disease for a long period of time, data processing is possible so that periodic test results can be accumulated and displayed, and the processed results can be provided to the user terminal 300 through an application. Accordingly, the user terminal 300 can be able to determine the prognosis for the disease and the expected treatment time.

The user terminal 300 can be, for example, a laptop, a smart phone, a tablet, or the like on which an application is installed.

The user terminal 300 can communicate (e.g., via wired or wireless communication) directly with the diagnostic device 200 or the server 400 through a network, and the diagnostic device 200 and the server 400 can also communicate directly through a network.

In this case, wireless communication technologies such as, IEEE 802.11 WLAN, IEEE 802.15 WPAN, UWB, Wi-Fi, Zigbee, Z-wave, and Bluetooth can be applied to the network, and can include a wireless communication unit 260 of each device (the user terminal 300 and the diagnostic device 200) to apply at least one or more communication technologies.

The wireless communication unit 260 can be changed depending on the communication method of other devices (the user terminal 300 and the diagnostic device 200) or the server 400 that is a target to communicate with.

As described above, in the biosensor system, the connection terminal 153 of the biosensor cartridge 100 accommodating the specimen is inserted into and electrically connected to the portable integrated biosensor diagnostic device 200 so that a detection signal is read.

The functional configuration of the biosensor diagnostic device 200 for reading the detection signal is shown in FIG. 2. Referring to FIG. 2, the biosensor diagnostic device 200 includes a plurality of function modules.

Each functional module can be individually packaged and accommodated in the case of one biosensor diagnostic device 200, and a plurality of functional modules can be packaged as one module and accommodated in a case 201, 202.

The biosensor diagnostic device 200 includes a signal conversion amplifier 210, a signal filtering unit 220, a signal processing unit 230, an operation unit 250, a wireless communication unit 260, a power supply unit 280, a display unit 290, a QR reader unit 270, and a sensor controller 240.

The signal conversion amplifier 210 first receives a detection signal transmitted from the biosensor cartridge 100, and converts and amplifies the current value of the detection signal so that the current value can be read by the biosensor diagnostic device 200.

The signal conversion amplifier 210 can have an analog circuit including a resistor that generates a voltage drop according to a changed current value which is a detection signal transmitted from the biosensor cartridge 100, and can further include an amplifying circuit that receives and amplifies such a voltage drop.

The amplified signal is transmitted to the signal filtering unit 220 to remove noise and then transmitted to the signal processing unit 230. The signal processing unit 230 can convert the amplified analog sensing value from which the noise has been removed into a digital value for a diagnostic operation, and can include an analog-digital converter (ADC) for this purpose.

As described above, the signal conversion amplifier 210, the signal filtering unit 220, and the signal processing unit 230 can all be implemented as a single integrated circuit chip. Such an integrated circuit chip can correspond to a cartridge insertion module 211 in FIG. 3.

The sensor controller 240 can provide a reference voltage whose level is changed according to the control of the operation unit 250 to the connection terminal 153 of the connected biosensor cartridge 100, and the biosensor cartridge 100 receives a reference voltage having a varied level from the sensor controller 240 and flows a current value changed by a varied resistance value of channel to the connection terminal 153. The connection terminal can be disposed at one side of the biosensor cartridge 100. The sensor controller 240 can be mounted together as a voltage level conversion circuit in the integrated circuit chip.

Meanwhile, the biosensor diagnostic device 200 includes an operation unit 250 for controlling the operation of the diagnostic device 200 and reading a received a digitized detection value.

The control of the diagnostic device 200 can include a separate controller (e.g., hardware-embedded processor), but it is possible to simultaneously read whether a detection value is detected and control the operation of the entire diagnostic device by executing a program stored in one controller.

In this case, the operation unit 250 can be implemented as a separate integrated circuit chip, and can be mounted in a main board 255.

The operation unit 250 can read whether there exists a target material for the detection value according to the reading program, process the result and provide the result to the display unit 290. In addition, such a reading result can be transmitted to a cloud server 400 and a user terminal 300 through a wireless communication unit 260.

The operation unit 250 can also control the operation of the diagnostic device 200 for the reading. For example, when the connection terminal 153 of the biosensor cartridge 100 is inserted into the cartridge insertion module 211, the operation unit 250 can detect the insertion and transmit a QR reading command to the QR reader unit 270.

Accordingly, the QR reader unit 270 performs an operation for reading the QR code attached to the rear surface of the biosensor cartridge 100 inserted into the cartridge insertion module 211, and transmits the information back to the operation unit 250.

The operation unit 250 receives the QR information, performs an certification request to the cloud server 400 accordingly, and when certification information is received from the cloud server 400 and confirmed as genuine, performs reading for the biosensor cartridge 100, and matches the reading result with the certification result of the biosensor cartridge 100 and processes it.

Accordingly, the operation unit 250 can reduce an error by minimizing a time difference of the result matching (e.g., minimizing the time to determine if the biosensor cartridge 100 is genuine) by simultaneously executing the module control of the diagnostic device 200 and the execution of the read program.

The operation unit 250 can include a memory card (e.g., flash memory) as a data storage unit, a library file for diagnosing biomaterials, and an embedded system board equipped with a signal processing device. For example, a memory card capable of storing output signal data is inserted into the embedded system board, and a system operating system (OS), driving program, library file for analysis, and the like are stored in the memory card. In addition, signal processing for concentration analysis of biomaterials is calculated through comparison analysis with library files in the central processing unit (CPU) of the embedded system board, and the analyzed result is stored again in the memory card. In addition, the wireless communication unit 260 can be mounted together in such an embedded system board, but is not limited thereto.

The biosensor diagnostic device 200 includes a display unit 290 as a user interface, and the display unit 290 includes a liquid crystal display device, an OLED or LED display device, a touch panel, and the like to display an analyzed result detected by creating a program considering a user's convenience. Various types of terminals, dials, buttons, and the like can also be provided as user interfaces.

A terminal 297, a dial 296, a button 294, and the like turn on/off the operation of the biosensor diagnostic device 200, and can be connected to the operation unit 250 to control the operation unit 250 according to a user command. That is, as a user's command is input in the interface 297, 296, 294, the diagnosis of the biosensor cartridge 100 can be started. The display unit 290 displays the progress process during the diagnosis process, and displays the diagnosis result after the completion of diagnosis.

The biosensor diagnostic device 200 can include a separate power supply unit 280 capable of applying power to a plurality of modules, and the power supply unit 280 includes a battery 281. Accordingly, it is possible to supply power to the internal module from the battery 281 and thus the device 200 can be portable. The battery 281 can be charged by an external power source, such as alternating current AC power available from the utility.

Hereinafter, a detailed structure according to an example of the biosensor diagnostic device 200 will be described with reference to FIGS. 3 and 4.

Figure 3:
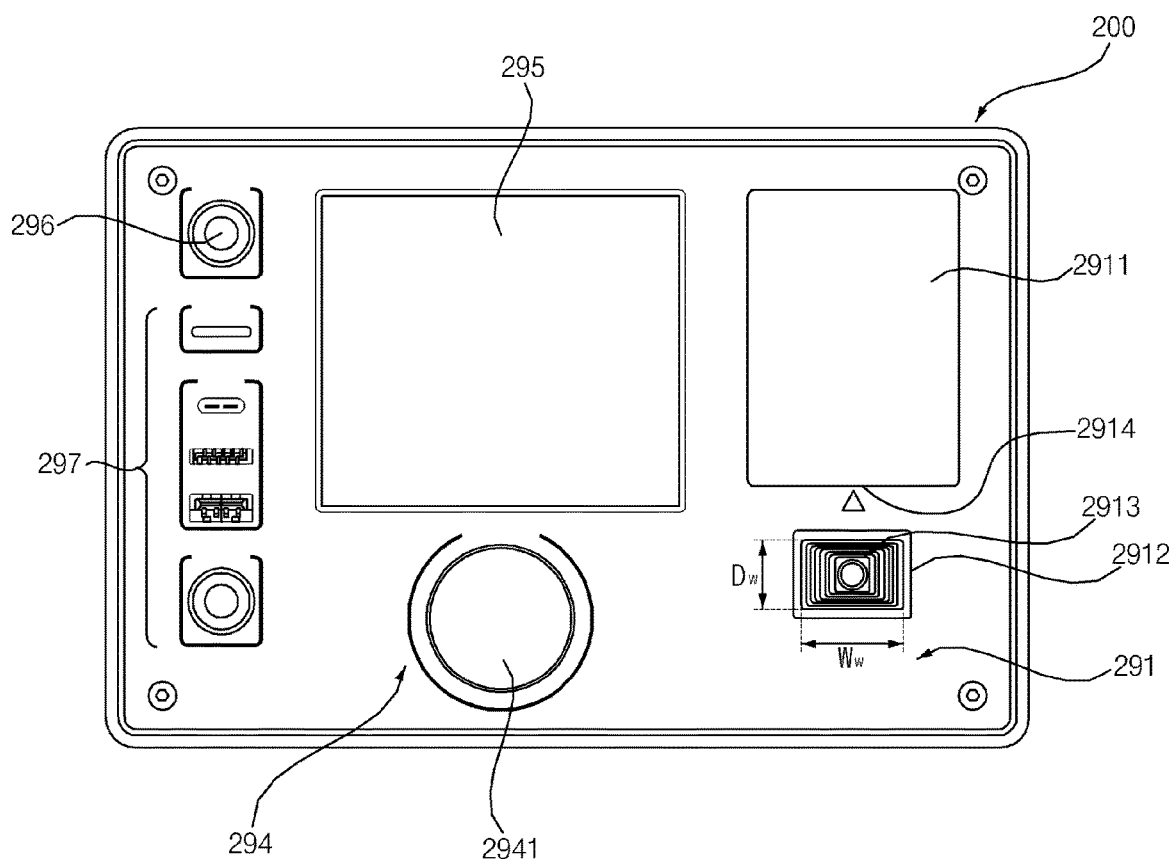
FIG. 3 is a front view of an example of the biosensor diagnostic device of FIG. 1.
Figure 4:
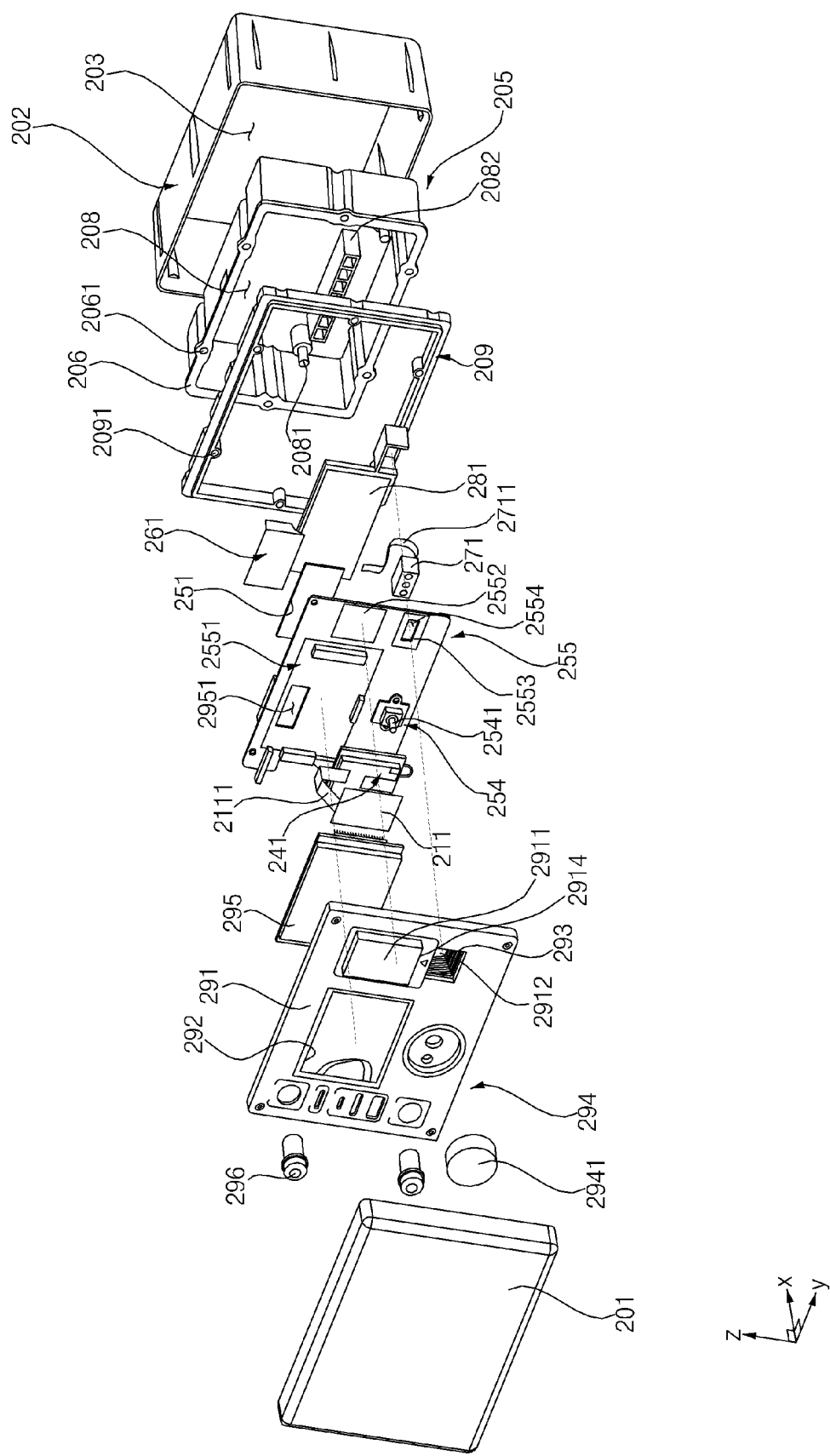
FIG. 4 is an exploded perspective view of the biosensor diagnostic device of FIG. 3.

FIG. 3 is a front view of an example of the biosensor diagnostic device 200 of FIG. 1, and FIG. 4 is an exploded perspective view of the biosensor diagnostic device 200 of FIG. 3.

Referring to FIGS. 3 and 4, the biosensor diagnostic device 200 according to the present embodiment is provided as a portable integrated device.

Here, the state of being integrated can include all states recognized as a single device in movement, disposition, and use of the diagnostic device 200. For example, the state of being integrated can mean that that it is located together inside the same case and is integrated by the same case, can mean that it is fixed by being fitted or attached to the same member and integrated by the same member, can mean that it is formed together in the same member to constitute a part of the same member, or can mean that it is wrapped or fixed together by the same member. On the other hand, it can be difficult to be considered as being integrated in the case of being connected by a separate output cable or the like.

The integrated biosensor diagnostic device 200 according to the present embodiment can include a separate inner cover 205 inside the case 201, 202. A front panel 291 is disposed to cover a plurality of modules accommodated in an accommodating portion 208 of the inner cover 205 and a front surface of the inner cover 205. In this case, one of a rear case 202 and the inner cover 205 can be omitted.

In the exploded perspective view of FIG. 4, the left side is defined as a front surface and the right side is defined as a rear surface along the X axis where the plurality of modules overlap, and the Y axis and Z axis perpendicular to the X axis are defined as two axes that forms a reference plane of the front panel 291 provided to a user.

The case 201, 202 of the biosensor diagnostic device 200 according to the present embodiment can include a front case 201 and a rear case 202. The rear case 202 is formed to have an accommodating portion 203 therein, and to have a bottom surface and a side surface. The accommodating portion 203 accommodates at least the inner cover 205, the main board 255 and the front panel 291. However, the accommodating portion 203 can accommodate all of the components of the diagnostic device 200 except for the front case 201.

The front case 201 and the rear case 202 can be disposed to face the accommodating portion 203 while the side surfaces are in contact with each other.

The accommodating portion 203 formed by the front case 201 and the rear case 202 is changed from an open space to a closed space according to the opening and closing of the front case 201.

An outer case accommodating the front case 201 and the rear case 202 simultaneously can be further formed. The outer case can be formed in a box type as shown in FIG. 3, can have a handle formed for easy portability, and have a pedestal formed to dispose the diagnostic device 200 at a certain angle.

The bottom surfaces of the front case 201 and the rear case 202 have the same size and define the total area of the biosensor diagnostic device 200.

The bottom surface can be formed in various shapes, and the shape can be a rectangle as shown in FIG. 4, but is not limited thereto, and can be a circle, an ellipse, a rhombus, or the like.

Meanwhile, when the shape of the bottom surface is a rectangle as shown in FIG. 4, the area is a portable size, and in the case of a polygon, one side can satisfy 30 cm or less, but it is not limited thereto, and it can be further miniaturized.

The height of the side surface forming the accommodating portion 203 of the rear case 202 can be greater than the height of the side surface of the front case 201, and the inner cover 205 is formed in the accommodating portion 203 of the rear case 202.

The inner cover 205 has the same shape as the rear case 202 so that it can be inserted into the accommodating portion 203 of the rear case 202, and the bottom surface of the inner cover 205 can have a smaller area than the rear case 202, but can be fitted to minimize a space between the side surface and the bottom surface of the rear case 202 and the side surface and the bottom surface of the inner cover 205.

The inner cover 205 serves as a cover that achieves a substantial integration, and when the case 201, 202 is damaged, the inner cover 205 can be separated from the case 201, 202 and replaced.

In addition, since the inner cover 205 is integrated with the rear case 202, one of the two can be omitted.

A plurality of modules are accommodated inside the accommodating portion 203 of the inner cover 205.

A supporter 2081, 2082 for supporting a module while defining the position of each module can be formed on the bottom surface of the inner cover 205, and the supporter 2081, 2082 can be variously designed depending on the disposition of the inner modules. The supporters 2081 and 2082 can be provided in plurality.

The main board 255 is accommodated in the accommodating portion 208 of the inner cover 205.

The main board 255 can be electrically connected to internal modules for executing a plurality of functions, and as shown in FIG. 4, a display module 295 constituting the display unit 290 and the cartridge insertion module 2911 in which the signal conversion amplifier 210 and the sensor controller 240 are integrated can be disposed in the front direction of the main board 255. In addition, a control switch 254 of the user interface of the front panel 291 can be disposed on the front surface.

An operation module 251 and a communication module 261 for controlling the operation of the control device and reading a detection signal according to a program can be disposed on the rear surface of the main board 255.

In addition, a QR reading module 271 can be disposed on the rear surface of the main board 255.

A battery 281 for applying power to the main board 255 and each of the functional modules is disposed, and the battery 281 can be disposed adjacent to the bottom surface of the inner cover 205.

Specifically, the front panel 291 includes a reference plane exposed on the front surface of the biosensor diagnostic device 200 as shown in FIG. 3.

The front panel 291 includes a first opening 292 for exposing a display module 295 that is disposed on the rear surface of the front panel 291 and displays an image on the front surface.

The first opening 292 can be covered with a transparent film, but is not limited thereto, and the display unit 290 of the display module 295 can be directly exposed.

A plurality of buttons, dials, and terminals 294, 296, 297 and the like for a user interface can be disposed around the first opening 291.

The plurality of buttons, dials, terminals 294, 296, 297, etc. can be adjusted in various forms according to design. For example, as shown in FIG. 3, a control dial 2941 can be disposed in a lower side of the first opening 292, and a plurality of terminals and dials 296 and 297 can be disposed also in the left side of the first opening 292, thereby receiving operation commands directly from a user.

Meanwhile, the cartridge insertion module 2911 is disposed in the right side of the first opening 292 in the front panel 291, and in the right side of the reference plane. Alternatively, the cartridge insertion module 2911 can be disposed in the left side of the first opening 292 in the front panel 291, and in the left side of the reference plane.

The cartridge insertion module 2911 protrudes from the reference plane to the front surface, and includes a terminal portion to be electrically connected by inserting the connection terminal 153 of the cartridge in the Z-axis direction.

Accordingly, a terminal portion is formed in a side surface of the insertion module 2911, and the terminal portion can include at least one insertion hole 2914.

The insertion hole 2914 can be implemented in various ways depending on the shape of the connection terminal 153 of the cartridge. When the connection terminal 153 of the cartridge is formed in an SD card chip type, a USB type such as USB-A, USB-C type, or a PIN type, correspondingly, it can be formed to read an electrode of the connection terminal 153.

In addition, when the plurality of insertion holes 2914 are formed so as to read various types of connection terminal 153, the plurality of insertion holes 2914 can be disposed in parallel along the X-axis direction in the side surface of the insertion module 2911.

A second opening 293 for exposing the QR reading module 271 is disposed in the lower side of the insertion module 2911.

The second opening 293 is formed in a position aligned with the rear surface of the housing 101 of the cartridge 100 in the X-axis direction in a state in which the connection terminal 153 of the cartridge is inserted into the insertion hole 2914 of the cartridge insertion module 2911.

The second opening 293 can be covered with a transparent film, and the second opening 293 can have a rectangular shape, but an area of the second opening 293 can be smaller than that of the first opening 292. Further, the second opening 293 can have any shape corresponding to a shape of the QR reading module 271 or a QR area 2553.

The second opening 293 serves as a passage through which the QR reading module 271 disposed on the rear surface reads the QR code of the cartridge 100 that is placed on the front surface. In the second opening 293, a light guide part 2912 protruding from the rear surface of the front panel 291 to form a sidewall of the second opening 293 in order to maintain a distance between the QR reading module 271 and the cartridge 100 is formed.

The light guide part 2912 can serve as an illumination for photographing of the QR reading module 271 while maintaining the distance of the QR reading module 271. That is, the light guide part 2912 can include a light guide plate formed on a sidewall of the second opening 293.

A main board 255 in which each module is mounted is disposed on the rear surface of the front panel 291, and the main board 255 can also have a shape similar to the bottom surface of the inner cover 205.

The main board 255 is divided into a display area 2551 in which the display module 295 is disposed in correspondence with (e.g., overlapping in a front-rear direction) the area division of the front panel 291, a cartridge area 2552 corresponding to (e.g., overlapping in a front-rear direction) the cartridge insertion module 2911, a QR area 2553 corresponding to the second opening 293, and a control area 254 corresponding to the button and the dial for a user interface.

The main board 255 is a circuit board on which a circuit is patterned on (e.g., layered on or printed on) the front and rear surfaces of the main board 255, and a connection terminal or a connector for electrical connection is disposed in each area. Each functional module can be integrated on the main board 255 after connecting the connection terminal of the board and connector and the connection terminal of each module or connector while being physically fixed in a defined area.

As shown in FIG. 4, a terminal module 241 in which the signal conversion amplifier 210, the signal filtering unit 220, and the sensor controller 240 are integrated is mounted in the cartridge area 2552 of the main board 255 corresponding to the cartridge insertion module 2911. The terminal module 241 can be connected to a insertion hole module 211 into which the connection terminal 153 of the cartridge is inserted by a flexible printed circuit board FPCB 2111, and unlike this, can be implemented as a single (e.g., unitary) component.

In addition, the display module 295 can be an LCD or LED panel module or any known type of display panel disposed in the display area 2551, and a terminal opening 2951 can be formed in the main board 255 in order to connect the operation module 251 on the rear surface of the main board 255 with the battery 281.

The operation unit 250 and the communication module 261 can also be connected to the main board 255 through a connector at the rear surface of the main board 255, but the disposition on the main board 255 is not limited thereto.

Meanwhile, the QR reading module 271 that reads a QR code through a QR opening 2554 formed in the QR area 2553 is disposed on the rear surface of the main board 255, and the QR reading module 271 is also electrically connected to the main board 255 through the flexible printed circuit board FPCB 2711 to receive power and control signals. That is, the QR reading module 271 can include the FPCB 2711 to electrically connect the QR reading module 271 to the main board 255.

A side frame 209 is formed for the disposition and fixing of such modules. The side frame 209 fixes the inner cover 205 and the front panel 291, and the inner cover 205 is fixed to the side frame 209 through a screw hole 2061 (or a plurality of screw holes 2061) extended from one end portion 206 of the side surface. Further, the side frame 209 is provided with multiple screw holes 2091 that overlap the screw holes 2061 of the inner cover 205. Fasteners, such as screws or bolts, pass through the screw home 2091 of the side frame 209, then are fixed to the screw holes 2061 of the inner cover 205. Each module is fixed at a specific position on the main board 255 through a plurality of other fixing parts, the main board 255 is physically fixed by coupling a screw and a screw hole between a plurality of fixing protrusions 2081 and 2082 protruding from the bottom surface of the inner cover 205 and the front panel 291.

Each module and component disposed therebetween is fixed by fixing the main board 255, the front panel 291, and the inner cover 205, and an electrical connection is maintained without being shaken during movement.

In addition, the front panel 291 and the inner cover 205 are fixed together through the screw hole and the screw of the side frame 209 to be integrated. Fixing and assembling of each component proceeds by the screw hole and the screw, thereby making it easy to disassemble and reassemble.

The front case 201, the rear case 202, the inner cover 205, and the front panel 291 can be formed of a resin such as polycarbonate or plastic for portability.

The biosensor diagnostic device 200 is, as shown in FIG. 3, provided to a user by exposing the front panel 291 in a form of having a space for accommodating a plurality of modules therein, and various external cases can be applied.

In particular, in the reference plane of the front panel 291 provided to a user as shown in FIG. 3, a screen of the display module 295 is provided, and various buttons and dials for a user interface are provided. In particular, a power button, a plurality of control buttons, and a USB terminal can be provided. In addition, the cartridge insertion module 2911 is provided to one side of the display module 295, and the connection terminal 153 is inserted into the insertion hole 2914 parallel to the reference plane of the panel 291, so that diagnosis of the biosensor cartridge 100 is possible.

Hereinafter, the biosensor cartridge 100 applied to the present embodiment will be described with reference to FIGS. 5 to 7.

Figure 5A:
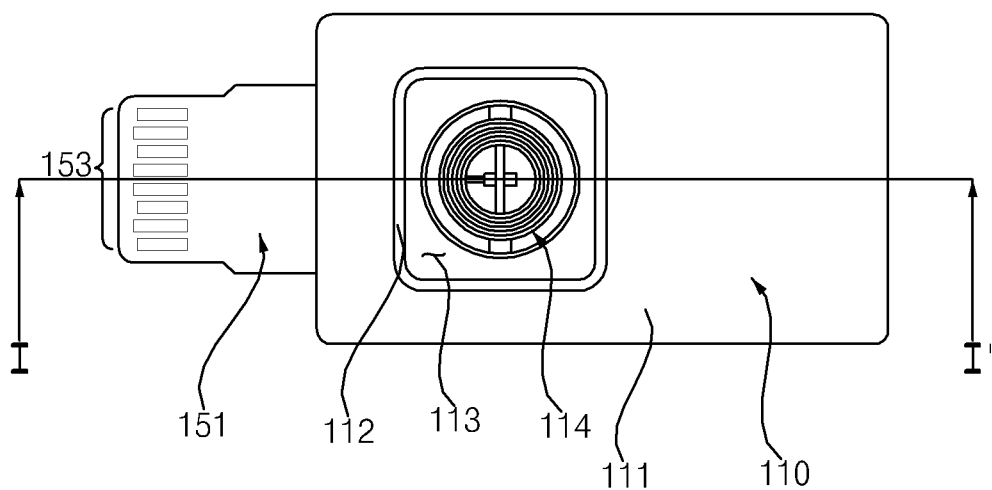
FIGS. 5A and 5B are respectively top and rear views of an example of the biosensor cartridge of FIG. 1.
Figure 5B:
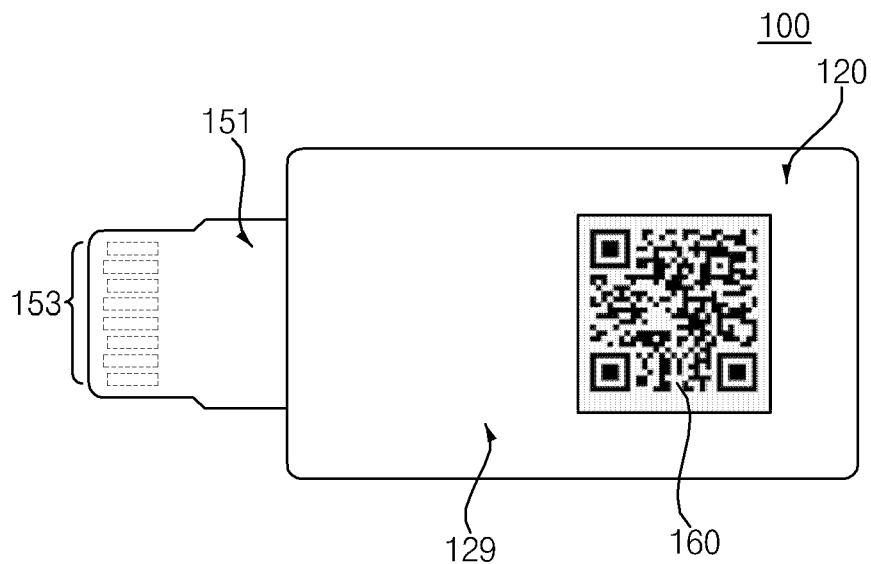
Figure 6:
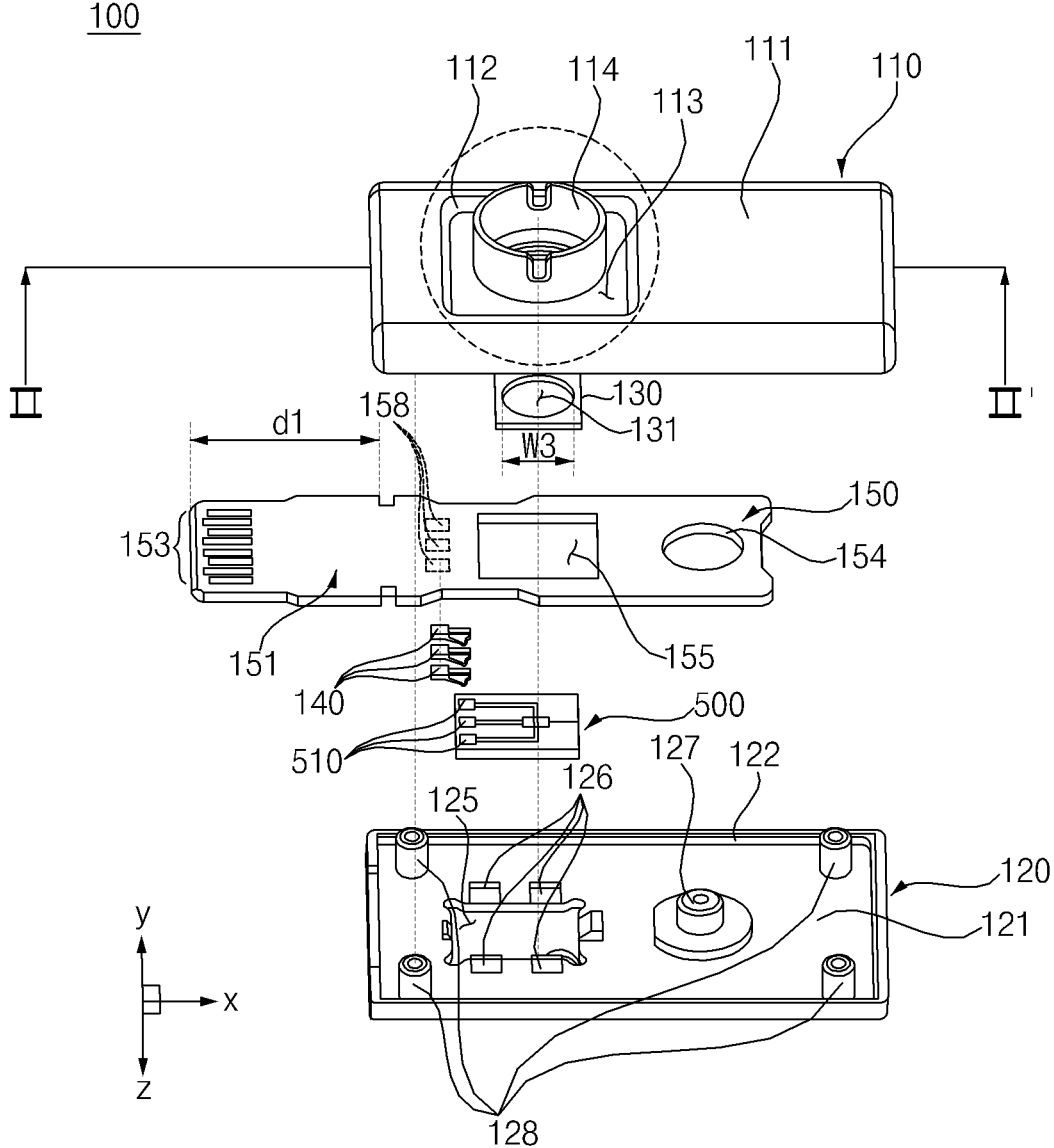
FIG. 6 is an exploded perspective view of an example of the biosensor cartridge of FIG. 1.
Figure 7:
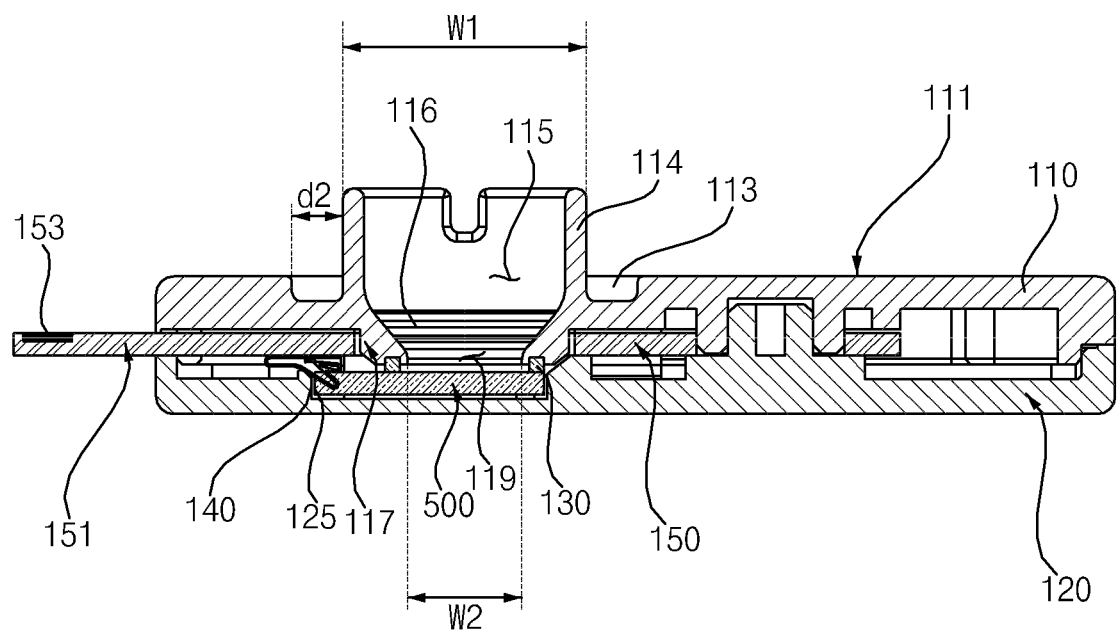
FIG. 7 is a cross-sectional view of the biosensor cartridge of FIGS. 5 and 6 taken along lines I-I' and FIG. 8 is a top view of an example of a sensor chip applicable to the biosensor cartridge of FIG. 6.

FIGS. 5A and 5B are top and rear views of an example of the biosensor cartridge 100 of FIG. 1, FIG. 6 is an exploded perspective view of an example of the biosensor cartridge 100 of FIG. 1, and FIG. 7 is a cross-sectional view of the biosensor cartridge 100 of FIGS. 5 and 6 taken along lines I-I' and II-II'.

Referring to FIGS. 5A to 7, the biosensor cartridge 100 according to the present embodiment accommodates a sensor chip 500 that generates an electrical detection signal according to a target material, and has a structure of including a connection terminal 153 capable of transmitting the detection signal to an external diagnostic device 200.

Specifically, the biosensor cartridge 100 is formed of a bar type housing 110, 120, a partial surface 151 of the circuit board 150 protrudes from the end surface of the side surfaces of the housing 110, 120, and a connection terminal 153 that is inserted into the external diagnostic device 200 and transmits the detection signal is formed on the partial surface 151 of the protruding circuit board 150.

The accommodating portion 119 for accommodating a specimen is formed on an upper surface 111 of the housing 110, 120, and a QR label 160 can be attached to the lower surface of the housing 110, 120.

The connection terminal 153, which protrudes from the side surface of the housing 110, 120 and is exposed, is disposed in the same direction as the lower surface of the housing 110, 120 and is not exposed when the cartridge 100 is viewed from the upper surface. Accordingly, it is possible to reduce the risk that the specimen flowing out of the accommodating portion 119 touches the connection terminal 153.

The biosensor cartridge 100 includes housing 110, 120, a sensor chip 500, and a circuit board 150.

The circuit board 150 is also formed in a bar type, and has one end where a connection terminal 153 is formed so that the connection terminal 153 of the circuit board 150 is coupled to be exposed to the outside of the housing 110, 120, thereby forming the entire shape of cartridge 100.

Specifically, the housing 110, 120 includes a lower housing 120 and an upper housing 110.

The lower housing 120 includes a bar-type bottom surface 121 (e.g., a planar shaped surface or a rectangular shape surface that is planar) and a side surface 122 surrounding the bottom surface 121. The bottom surface 121 includes a plurality of coupling protrusion 127, 128 protruding toward the upper housing 110, and the coupling protrusion 127, 128 is fitted with a coupling groove of the upper housing 110 so that the upper and lower portions of the housing 110, 120 are coupled and integrated. The lower housing 120 can include four coupling protrusions 128 positioned at corners of the lower housing 120, which are coupled to corresponding grooves of the upper housing 110 which are located at corners of the upper housing 110. The coupling protrusion 127 (e.g., substrate protrusion) can be from the other coupling protrusions 128 (e.g., corner coupling protrusions 128). Alternatively, more than four coupling protrusions 127 can be formed and the coupling protrusions can be equally spaced around a periphery of the lower housing 120.

A substrate protrusion 127 defining a position while fixing the circuit board 150 toward the upper housing 110 is formed on the bottom surface 121 of the lower housing 120, and a plurality of sensor protrusions 126 defining a chip area 125 in which the sensor chip 500 is disposed are formed in one side of the lower housing 120, the one side facing the upper housing 11.

The sensor protrusion 126 is disposed to correspond to the size of the sensor chip 500 so as to define a chip area 125 in which the sensor chip 500 is disposed, and is formed to have a certain elasticity (e.g., predetermined elasticity) so that the sensor chip 500 can be fitted. Each sensor protrusion 126 has a protruding structure having an inclination toward the chip area 125 so that it is not damaged by the edge of the sensor protrusion 126 when the sensor chip 500 is mounted. However, since the sensor protrusion 126 does not electrically connect the sensor chip 500, it can be implemented in various forms, and can be formed as a rail structure for sliding coupling in addition to fitting.

A sensor chip 500 is disposed in the chip area 125.

The sensor chip 500 is a semiconductor-based biosensor, and is divided into a sensor area 540 that reacts according to a target material in the specimen through contact with the specimen, and a pad area 510 for transmitting a detection signal generated according to the sensor area 540 to the circuit board 150.

The pad area 510 can be patterned to be disposed in one side of the sensor chip 500 as shown in FIG. 6, and accordingly, the electrical connection between the circuit board 150 and the sensor chip 500 is performed in the pad area 510.

The sensor chip 500 can have different sizes depending on the size of the cartridge, for example, can have a rectangular shape of 8 mm*6 mm, or can have a square shape of 6 mm*6 mm. The size of the sensor chip 500 can be variously implemented according to the performance of the sensor chip 500 or the purpose of the sensor chip 500.

The detailed structure of the sensor chip 500 will be described in detail later.

The circuit board 150 is disposed on the sensor chip 500.

The circuit board 150 can be provided as a rigid board like a printed circuit board (PCB), and the sensor chip 500 is electrically/physically bonded to the lower portion.

The circuit board 150 includes a sensor opening 155 through which a sensor area 540 of the sensor chip 500 is exposed, and the sensor opening 155 has a size smaller than that of the sensor chip 500. In addition, the sensor opening 155 can have a size corresponding to the sensor area 540 of the sensor chip 500, and has a size to expose the sensor area 540.

The circuit board 150 further includes a protrusion hole 154 through which the substrate protrusion 127 of the lower housing 120 penetrates to fix the circuit board 150, and accordingly, the circuit board 150 and the lower housing 120 are fixed.

The circuit board 150 can be implemented by a plurality of circuit patterns patterned on a base member (not classified by reference numerals, denoted by 150 in the drawing) as the deposition structure thereof, and an insulating layer covering the circuit pattern.

The circuit pattern and the insulating layer can be formed on a rear surface of the base member, and a reinforcing plate can be attached to the front surface of the base member. A rear surface of the circuit board 150 can be defined as a surface facing the lower housing 120, and a front surface of the circuit board 150 can be defined as a surface facing the upper housing 110.

The required strength at the time when a part of the circuit board 150 is used as the connection terminal 153 that is inserted into the diagnostic device 200 can be satisfied by attaching the reinforcing plate to the rear surface of the circuit board 150 as described above.

On the rear surface of the circuit board 150, a circuit pattern including a plurality of connection pads 158 for connecting to the sensor chip 500 is formed, and a circuit pattern that extends to the connection pad 158 to transmit the detection signal from the connection pad 158 to the external diagnostic device 200 is formed to be connected to the connection terminal 153 of the front surface.

The circuit board 150 can be patterned on both sides to be electrically connected to each other.

Accordingly, the number of connection terminal 153 on the front surface of the circuit board 150 can be equal to or greater than the number of pads of the sensor chip 500.

The plurality of connection terminals 153 can be spaced apart from each other at one end of the exposed surface 151 of the circuit board 150, i.e., at one end of the circuit board 150 and disposed in parallel.

For example, when the sensor chip 500 has three pads, the number of the connection pads 158 of the circuit board 150 also satisfies three, and the number of the connection terminal 153 satisfies three or more.

The connection terminal 153 further includes terminals not electrically connected to each connection pad 158 and can be used as a terminal for electrostatic discharge (ESD) blocking.

As shown in FIG. 6, the circuit pattern patterned on the front surface of the circuit board 150 can include eight connection terminals 153. In such a connection terminal 153, when the sensor chip 500 is driven in multi-channel to be connected to a plurality of connection pads 511 and to transmit and receive signals, four connection terminals can be allocated as a connection terminal 153 for transmitting and receiving signals of each pad by connecting to the source pad, drain pad, and gate pad of the sensor chip 500 corresponding to each channel, and four connection terminals are applicable as a terminal for ESD and incoming detection signal generation.

Such a connection terminal 153 can be formed as an SD card pin type or a USB-A type depending on an embodiment, but a USB-C type having more terminals can also be utilized. Preferably, the connection terminal 153 can be implemented as an SD card pin type, and more terminals than FIG. 5 can be implemented. Thus, the number of pads of the connection terminal 153 can increase in proportion to the number of probe material applied to the sensor chip 500, i.e., the number of source electrodes (or the number of drain electrodes).

Meanwhile, the circuit board 150 includes a plurality of coupling grooves, and the plurality of coupling grooves are formed to be able to fit while specifying a position when the upper housing 110 and the lower housing 120 are coupled.

Meanwhile, the upper housing 110 has a structure where the upper surface 111 and the rear surface are different from each other as shown in FIG. 6.

The upper housing 110 faces the lower housing 120 and is coupled to the lower housing 120 and serves as an upper case capable of accommodating the circuit board 150 and the sensor chip 500 therein. In addition, an accommodating portion 119 exposing the sensor area 540 of the sensor chip 500 is formed in the upper housing 110 to accommodate a test target specimen.

The upper housing 110 is formed to have rigidity that can firmly support the connecting member 140 by pressing the connecting member 140 with a certain force. The connecting member 140 can be formed in plurality and can be conductive tabs (e.g., metal tabs) for connecting the connection pad 158 disposed on the circuit board 150 with the pads 511 of the sensor chip 500.

The upper housing 110 and the lower housing 120 can be configured to surround the surfaces of the sensor chip 500 and the circuit board 150 to protect the sensor chip 500 and the circuit board 150 from the outside. Due to the strong coupling between the upper housing 110 and the lower housing 120, the specimen provided to the sensor chip 500 through the accommodating portion 119 can be prevented from leaking into the housing 110, 120.

At this time, when the upper housing 110 and the lower housing 120 are coupled, an opening through which the connection terminal 153 of the circuit board 150 protrudes is formed in one side (e.g., a first side) of the side surface, e.g., in a cross-section, so that the connection terminal 153 is exposed to a cross-section, and is inserted into the insertion hole 2914 of the external diagnostic device 200 as the connection terminal 153 of the cartridge.

The accommodating portion 119 for exposing the sensor area 540 of the sensor chip 500 and accommodating a specimen is formed on the upper surface 111 of the upper housing 110. The accommodating portion 119 is a space for inducing a reaction with the exposed sensor area 540 by accommodating a test target specimen in a fluid state, e.g., in a liquid state, and the accommodating portion 119 forms a conical channel whose diameter becomes narrower as it approaches the sensor area 540 from the upper surface 111.

The accommodating portion 119 of the upper housing 110 receives a liquid specimen, and the specimen is randomly put into the accommodating portion 119. Thus, it is difficult to control an input amount of the specimen.

That is, when a large amount of specimen is put into the accommodating portion 119 for a quick and accurate reaction, there is a risk that the specimen can flow into an area out of a guard 114 of the accommodating portion 119 depends on a size of the biosensor cartridge 100 and a limited accommodating volume of the accommodating portion 119.

The guard 114 is for preventing the specimen of the accommodating portion 119 from flowing to the outside of the guard 114. The guard 114 can be formed in a cylindrical shape, and is formed to surround the opening of the upper surface 111 of the upper housing 110 and protrude upward (in the y-axis) from the upper surface 111.

Accordingly, the diameter W1 of the guard 114 can be the same as the diameter of the opening of the upper surface 111.

A guard groove 113 of a certain depth is formed on the upper surface 111 of the upper housing 110 while surrounding the accommodating portion 119. The guard groove 113 prevents the specimen overflowing from the accommodating portion 119 from flowing out of the housing 110, and is formed to be recessed by a certain depth from the upper surface 111.

The guard groove 113 can be formed in a circular shape identical to the shape of the guard 114, but can be formed in a rectangular shape having a minimum distance d2 or more from the guard 114 as shown in FIGS. 6 and 7. The guard groove 113 includes a vertical wall 112 defining an outer periphery of the guard groove 113.

As such, when the specimen flows to the outside, there is a risk that it can contact any dangerous pathogen, which is fatal to a user. In addition, since the specimen possibly flowing to the outside is in a liquid state, introduction of the specimen into the diagnostic device or contact thereof with the connection terminal 153 can cause damage to electronic devices.

Therefore, in this embodiment, even when a small amount of specimen is introduced, all specimens are collected into the sensor area 540 of the sensor chip 500 exposed by a lower opening of the accommodating portion 119, thereby inducing a sufficient reaction.

the sensor area 540 of the sensor chip 500 is exposed upward by the sensor opening 115 of the circuit board 150, and the lower opening of the accommodating portion 119 aligns with the exposed sensor area 540. The area of the accommodating portion 119 closest to the sensor area 540 is called the distal end, and the area furthest from the sensor area 540, which is opposite to the distal end, is considered the opening or outermost area. The distal end has a diameter W2 that is smaller than the diameter W1 of the opening/outermost area.

At this time, the opening 115 of the circuit board 150 is fitted to surround the rear surface of the inclined surface 116 of the accommodating portion 119, thereby fixing the positions of the circuit board 150 and the upper housing 110.

In addition, to this end, the rear surface of the inclined surface 116 of the accommodating portion 119 is formed to have a vertical step 117 in an area where it meets the opening 115 of the circuit board 150.

That is, the rear surface of the inclined surface 116 of the accommodating portion 119 forms an inclined portion along the inclined surface 116 at an angle equal to or greater than the inclination angle of the inclined surface 116 of the accommodating portion 119, and is inclined at an angle equal to or greater than the inclined surface 116 to form a space coupled to the circuit board 150.

At this time, at a portion to which the sensor opening 155 of the circuit board 150 is coupled, a step 117 corresponding to the cut surface of the sensor opening 155 of the circuit board 150 can be formed for fitting with the sensor opening 155 of the circuit board 150. Accordingly, the step 117 can be formed perpendicular to a horizontal plane (x-axis on which the sensor chip is placed).

The step 117 can have a spaced distance from the side surface of the sensor opening 155 of the circuit board 150, but is not limited thereto, and can be fitted and coupled.

It is easy to fix the circuit board 150 in case of being fitted and coupled without a separation distance, but a separation distance can be formed for tolerance.

In addition, when the rear surface of the circuit board 150 is placed in the lower housing 120, a separation distance for tolerance can be ensured from the rear surface of the upper housing 120.

As described above, the front surface of the circuit board 150 and the rear surface of the upper housing 110 can be coupled with a certain tolerance distance to prevent distortion of the circuit board 150, and to be applied as a buffer for an error in the process to reduce the defect rate.

In addition, even if the separation distance for such a tolerance is included, the circuit board 150 and the housing 110, 120 can be clearly coupled by combining with the upper and lower housings 110 and 120 by a plurality of coupling grooves and coupling holes.

Accordingly, the circuit board 150 is firstly fixed while the step 117 of the rear surface of the accommodating portion 119 and the sensor opening 115 of the circuit board 150 are fitted, and is secondarily fixed while the fixing protrusion 127 of the lower housing 120 and the fixing hole 154 of the circuit board 150 are coupled, so that the position is specified.

Meanwhile, a sealing part 130 can be further formed between the upper housing 110 and the sensor area 540. The sealing part 130 can be elastic, and formed of a rubber, fluorinated rubber, silicon, neoprene, nitrile, polyvinyl chloride (PVC), thermoplastic polyurethane, polytetrafluoroethylene and the like.

The sealing part 130 is formed as a separate element as shown in FIG. 6, and is coupled and compressed at the time of the housing 110, 120 coupling, thereby preventing the specimen from flowing to the outside of the sensor area 540.

In this case, the sealing part 130 can have a sealing opening 131 having a diameter w3 larger than the diameter w2 of the rear opening of the accommodating portion 119 as shown in FIG. 6, and the rear opening and the sealing opening 131 can be disposed to have a concentric circle. Accordingly, when assembling, as shown in FIG. 7, the sealing part 130 is disposed outside the lower opening of the accommodating portion 119 to form a concave groove.

This is designed to avoid danger that the elastic sealing part 130 is pushed to the sensor area 540 by the compression of the sealing part 130 and covers the sensor area 540 in contact with the specimen, as a tolerance is set when the sealing part 130 is compressed.

As described above, it is possible to ensure the sealing of the specimen while securing the area of the sensor area 540 by adjusting the size of the sealing opening 131 of the sealing part 130 and the opening size of the accommodating portion 119.

Meanwhile, the sealing part 130 can be a closed cell type waterproof pad having elasticity, but is not limited thereto.

Meanwhile, the connection pad 158 formed on the rear surface of the circuit board 150 is formed in the same number as the pad 511 of the sensor chip 500, and a connecting member 140 is disposed for electrical and physical connection between the connection pad 158 of the circuit board 150 and the pad 511 of the sensor chip 500.

As shown in FIG. 6, the connecting member 140 can be formed separately for each pad 158, and can be formed as a clip-type elastic contact piece. Such a connecting member 140 can be a C-clip or a spring terminal.

Each connecting member 140 can include a first surface in contact with the pad area 510 of the circuit board 150 and a second surface configured to be elastically deformable by being bent in the length direction of the first surface from one side surface of the first surface.

The first surface is formed to have a certain length and is in contact with the pad area 510 of the circuit board 150, and the second surface is in contact with the pad 511 of the lower sensor chip 500 and elastically deformed.

To this end, in the state where the connection pad 158 of the circuit board 150 and the first surface are in contact with each other through welding or soldering, when the circuit board 150 is disposed in the lower housing 120 in which the sensor chip 500 is disposed, a bending portion is elastically deformed as pressure is applied vertically (e.g., substantially vertically) to the connecting member 140 by assembling the upper housing 110 and the lower housing 120.

At this time, the angle is changed so that the second surface is parallel to the first surface as a spring coupling portion is pushed into the inside of the second surface. Thus, the second surface is in contact with the pad 510 of the sensor chip 500 to maintain a conducting state, so that physical coupling and electrical coupling occur simultaneously.

As described above, since the probe material in the sensor chip 500 is not exposed to high temperature in a bonding process by performing electrical connection of the sensor chip 500 with the circuit board 150 without a separate bonding process, it is possible to prevent a problem that protein modification occurs.

That is, in the presence of probe material vulnerable to heat due to the characteristics of the biosensor, the characteristics of the probe material can be maintained by excluding a heating process, and electrical connection between the sensor chip 500 and the circuit board 150 becomes possible.

Meanwhile, on the rear surface 129 (see FIG. 5B) of the lower housing 120 of the biosensor cartridge 100, i.e., the rear surface 129 of the cartridge 100 exposed to the outside, a QR label 160 including a QR code in which sensor information including a product ID and a manufacturing serial number for genuine product certification of the biosensor cartridge 100 is stored is attached.

The QR code can be attached to the central area of the rear surface 129 of the lower housing 120 so that the rear surface 129 of the lower housing 120 of the cartridge 100 can be aligned over the second opening 293 which is the QR opening when the cartridge 100 is coupled with the external diagnostic device 200.

The QR code can include all sensor information for genuine product certification. As an example, it can include sensor chip 500 information and cartridge information as well as the product ID and manufacturing serial number. The information of the sensor chip 500 can include probe material activated in the sensor chip 500, a disease to be diagnosed, a manufacturing date, a manufacturing location, and a manufacturing serial number of the sensor chip 500. In addition, the cartridge information can include an assembly date, a test date, and a sensor ID of the biosensor cartridge 100.

The stored QR code is read from the QR reading module 271 of the diagnostic device 200 at the same time when it is inserted into the diagnostic device 200, and a process for genuine product certification can be performed with the cloud server 400.

The biosensor cannot determine whether it is an imitation or not. Even if it is genuine, sensor errors are often found or decided from accumulated test data after manufacturing and sales. Therefore, a process of classifying the biosensor cartridge 100 in which an error has occurred is required before the test proceeds.

In the case of the biosensor cartridge 100, it is possible to check an error including a current risk to a corresponding type of the biosensor cartridge 100 through such a certification procedure.

The biosensor cartridge 100 according to the present embodiment does not include a separate memory chip for storing sensor-specific information for such a certification procedure.

When such a memory chip is separately included, the size of the circuit board 150 increases, and the size of the housing 110, 120 increases according to the size of the circuit board 150. In addition, as the circuit of the circuit board 150 becomes complicated, the number of pins used in the connection terminal 153 increases, thereby causing problems in miniaturization and cost of the cartridge 100.

Like the biosensor cartridge 100 according to the present embodiment, by attaching a QR label 160 on which a QR code is printed to the rear surface of the housing, such that a memory chip can be replaced (e.g., a memory chip is not necessary), and the time difference between reading of the sensor result and certification can be minimized by reading the QR code almost simultaneously (e.g., simultaneously) with the coupling of the cartridge 100 and the diagnostic device 200.

Such a QR code can be prevented from being arbitrarily attached and detached by attaching it as a security label 160, such as a VOID label, on the rear surface of the lower housing 120.

In such a biosensor cartridge 100, in a state in which the sensor chip 500 is placed in the lower housing 120, the upper housing 110 coupled to the circuit board 150 to which the connecting member 140 is attached is pressed for assembling with the lower housing 120, so that the sensor chip 500 and the circuit board 150 are physically and electrically attached and fixed.

In this case, the attachment of the upper housing 110 and the lower housing 120 can be further strengthened by performing fusion on an edge attachment area of the upper housing 110 and the lower housing 120.

Such fusion can be performed by ultrasonic fusion, but is not limited thereto, and can be performed through a separate adhesive member.

The edge attachment area formed as described above is continuously formed in the entire edge excluding an open portion through which the connection terminal 153 protrudes, i.e., in the distal end of the side surfaces of the upper housing 110 and the lower housing 120, thereby preventing moisture or foreign substances from penetrating into the interior from the outside.

Hereinafter, the biosensor chip 500 of the present embodiment will be described with reference to FIGS. 8 to 11.

Figure 8:
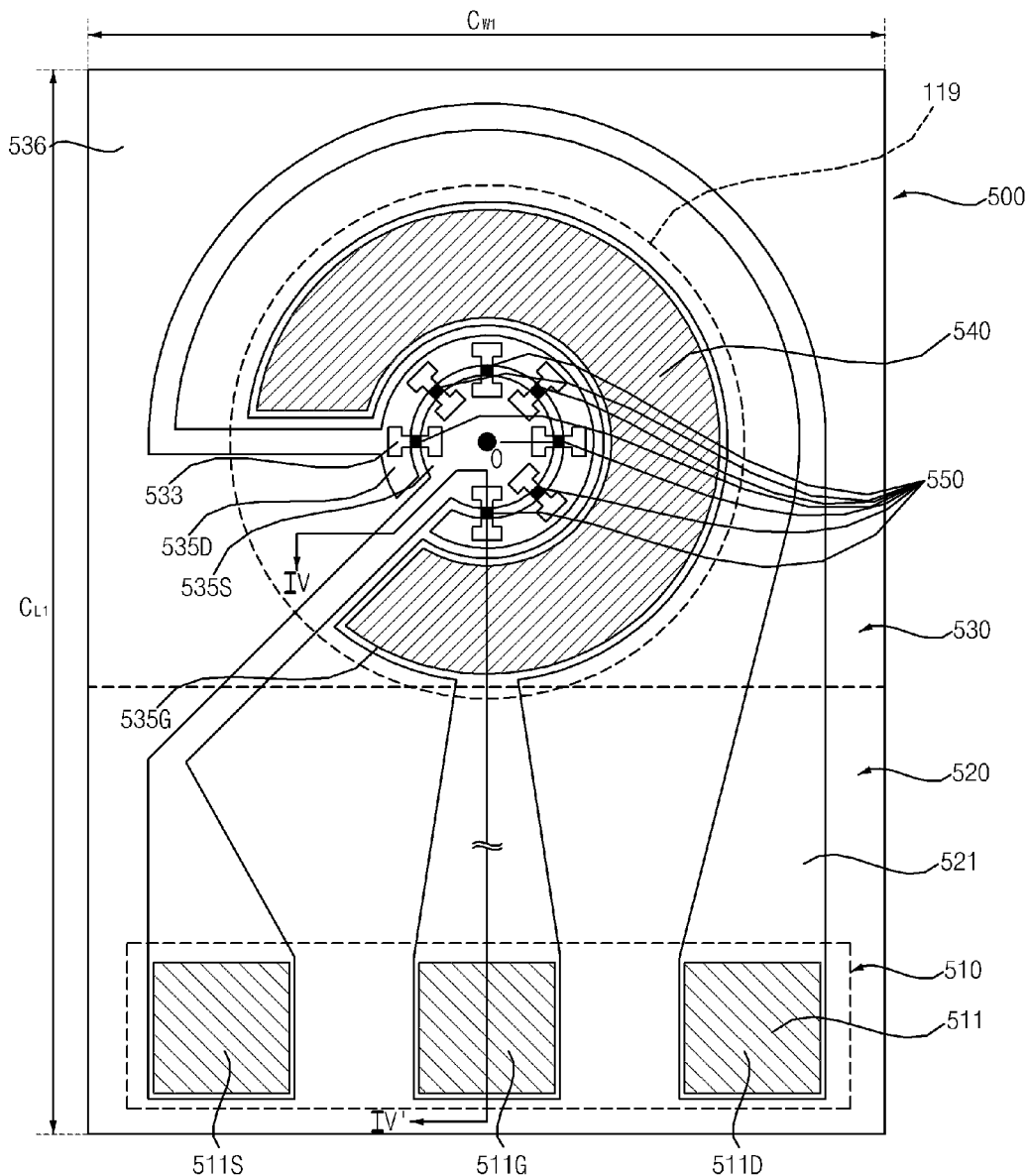
Figure 9:
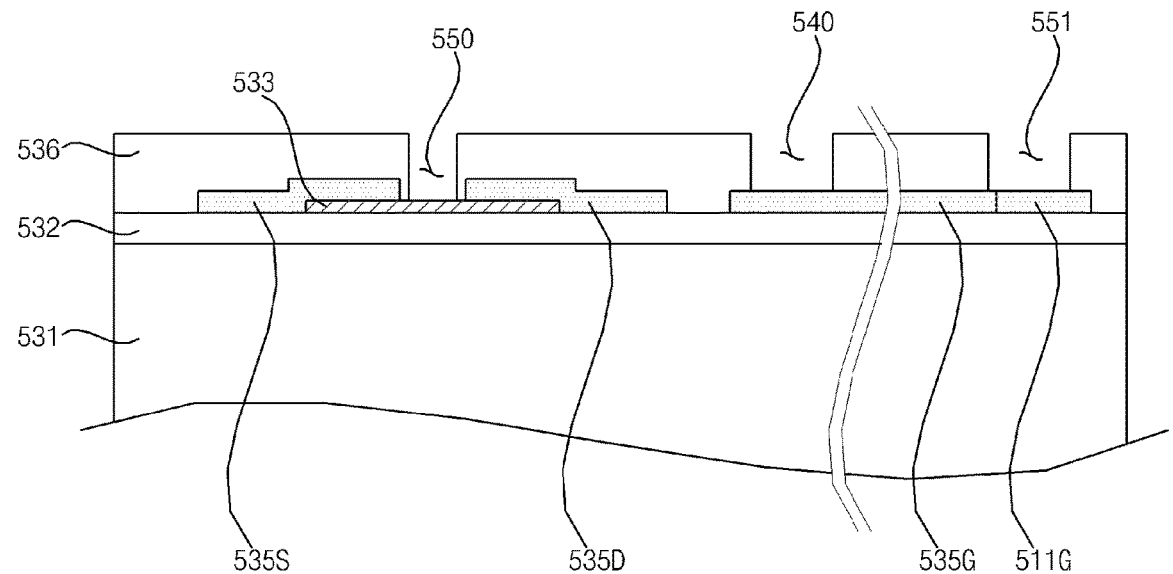
FIG. 9 is a cross-sectional view of the sensor chip of FIG. 8.
Figure 10A:
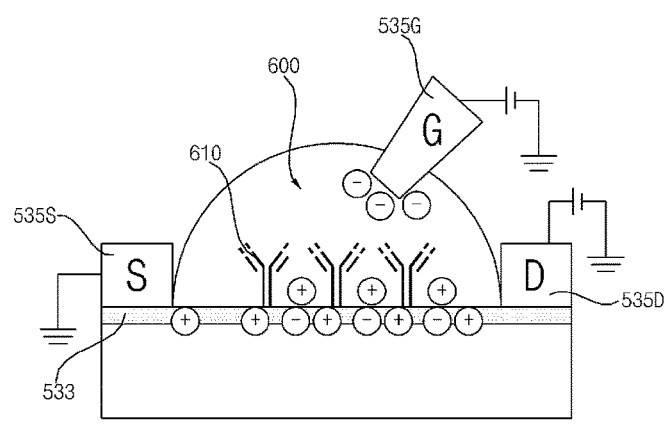
FIGS. 10A and 10B are schematic diagrams illustrating a reaction of the sensor chip of FIG. 8 according to a target material.
Figure 10B:
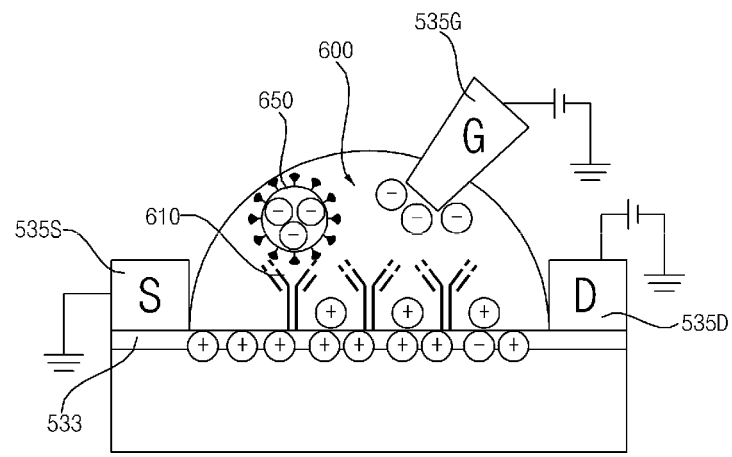
Figure 11:
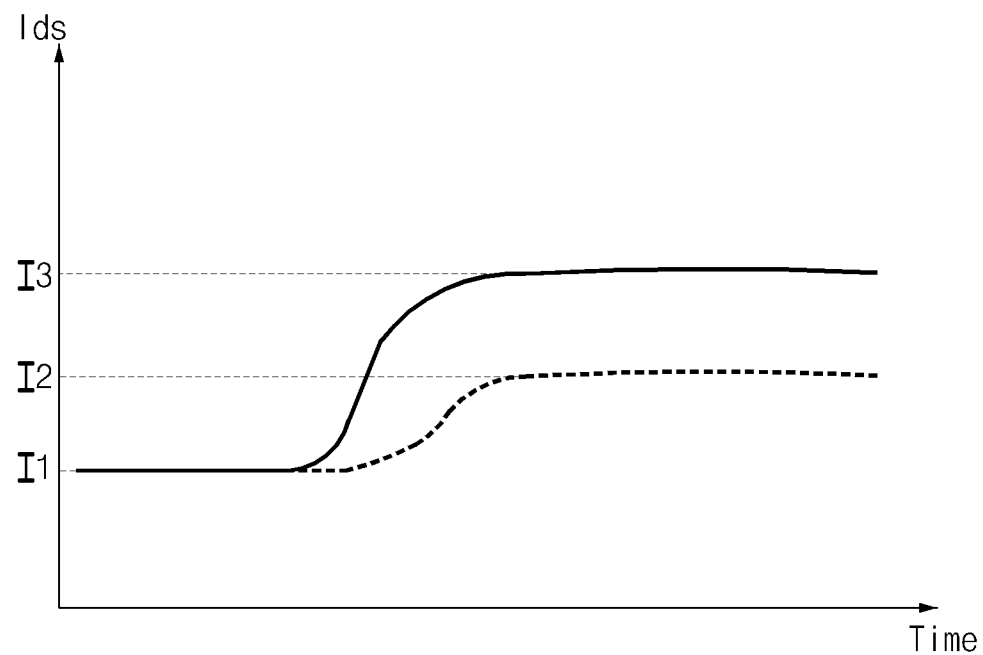
FIG. 11 is a graph illustrating a change in output current of the sensor chip according to FIGS. 10A and 10B.

FIG. 8 is a top view of an example of a sensor chip applicable to the biosensor cartridge of FIG. 6, FIG. 9 is a cross-sectional view of the sensor chip 500 of FIG. 8, FIGS. 10A and 10B are schematic diagrams illustrating a reaction of the sensor chip of FIG. 8 according to a target material, and FIG. 11 is a graph illustrating a change in output current of the sensor chip according to FIGS. 10A and 10B.

The biosensor chip 500 detects a target material from the specimen introduced into the interior by the accommodating portion 119 of the biosensor cartridge 100, and transmits an electrical signal generated by reacting with the detected target material to the pad 158 of the circuit board 150 through the electrode pad 511.

For example, the specimen can refer to saliva, a body fluid including sweat, blood, a solution diluted with serum or plasma, and the like, as a biological material.

The biosensor chip 500 is a semiconductor-based sensor chip 500, and can be manufactured as a biosensor chip 500 to which graphene is applied.

The sensor chip 500 can have various sizes depending on the type of target material, the number of target materials, and the size of the cartridge 100, and can have, for example, the width ($C_{W1}$) of the chip 200 and the length ($C_{L1}$) of the chip 500 have a size of 6*6 mm or 6*8 mm.

Referring to FIGS. 8 to 12, the biosensor chip 500 according to the present embodiment can have a quadrangle shaped plane, have a front surface on which a sensor area 540 exposed to the outside through the accommodating portion 119 is formed, and be partitioned into a pad area 510 which is spaced apart from the sensor area 540 and connected to the pad 158 of the circuit board 150 through the connecting member 140, and a connection portion 520 connecting the sensor area 540 and the pad area 510.

The sensor area 540 detects a target material from the contacted specimen, and probe material that react with the target material to generate an electrical signal, e.g., an antigen, an antibody, an enzyme, and the like are attached thereto.

When the sensor area 540 comes into contact with a specimen, it interacts with a target material included in the specimen to generate an electrical signal. Accordingly, the external diagnostic device 200 connected to the biosensor 100 can analyze an electrical signal generated from the biosensor 100 to detect the presence or concentration of the target material.

The sensor area 540 includes a transistor structure, and has a structure where probe material is attached to a channel area 550 of the transistor.

Specifically, the sensor area 540 includes a plurality of circular or ring-shaped electrodes 535S (source electrode), 535D (drain electrode), and 535G (gate electrode) forming a concentric circle, and a plurality of channel areas 550 are formed between the plurality of electrodes 535S, 535D, and 535G, particularly, between the source electrode 535S and the drain electrode 535D.

An insulating layer 532 is formed on the semiconductor substrate 531, and the insulating layer 532 can be formed of oxide or nitride. When the semiconductor substrate 531 is a silicon substrate, the insulating layer 532 can be formed of silicon oxide or silicon nitride, and can be formed by various methods. For example, a silicon oxide layer can be formed on the surface through heat treatment.

A plurality of channels 533 are formed on the insulating layer 532 to be spaced apart from each other.

A plurality of channels 533 are disposed spaced apart by a certain distance from the center O of the accommodating portion 119 of the sensor area 540, and a central area of each channel 533 is exposed to form the channel area 550.

That is, the plurality of channels 533 are disposed to be spaced apart from each other on the circumference of an imaginary circle having a certain length as a radius in the center O of the circle.

The plurality of channels 533 can be disposed to be spaced apart by the same angle θ1. For example, as shown in FIG. 10, seven channels 533 can be formed, and each channel 533 can be spaced apart at an angle of 45 degrees.

Alternatively, five channels 533 can be disposed so that each channel 533 can be spaced apart at an angle of 60 degrees. However, the channels 533 can be spaced apart by any angle.

Each channel 533 can be patterned in a specific shape and can be made of a semiconductor material. However, unlike this, one channel can be formed of a graphene-based material that is highly reactive as a highly conductive material.

The channel 533 includes areas overlapping with the source and drain electrodes 535S and 535D, and a channel area 550 exposed to the outside through the accommodating portion 119 between the two overlapping areas.

The channel area 550 can be formed in an I-shape to have a narrower width than that of an overlapping area as shown in FIG. 8, and thus, a lower resistance can be provided in the channel area 550. However, aspects of the present disclosure are not limited thereto, and the channel area 550 can be formed in a bar-type to have the same width from the overlapping area to the channel 533.

A source electrode 535S having a shape of a smallest circle can be formed on a center O of the circle of the sensor area 540. The source electrode 535S can be formed as a circle having a smallest diameter. In addition, the source electrode 535S is formed to overlap one end of the channel 533, and simultaneously overlaps with a plurality of channels 533 to simultaneously supply a source voltage to the plurality of channels 533.

A drain electrode 535D can be formed outside the channel area 550 to be spaced apart from the source electrode 535S.

The drain electrode 535D can be formed in a ring shape, and is formed along the circumference of an imaginary circle that surrounds the channel area 550 and has a larger diameter than that of the channel area 550.

The drain electrode 535D can also simultaneously overlap with the plurality of channels 533 to simultaneously receive current from the plurality of channels 533.

One end of the drain electrode 535D is cut to form a channel through which a connection portion 521 of the source electrode 535D passes.

A gate electrode 535G is formed along the circumference of an imaginary circle having a larger diameter surrounding the drain electrode 535D.

The gate electrode 535G has the largest area and can occupy ½ to ⅔ of the sensor area 540. The gate electrode 535G is formed to be spaced apart from the source electrode, the gate electrode 535S, 535D, and the channel area 550.

One end of the gate electrode 535G is disconnected to also form a channel so that the connection portion 521 of the drain electrode and the source electrode 535S, 535D is connected to the pad(s) 511. Specifically, the source electrode 535S is electrically connected to a source pad 511S, the drain electrode 535D is electrically connected to the drain pad 511D and the gate electrode 535G is connected to the gate pad 511G, as illustrated in FIG. 8.

The electrodes 535S, 535D, and 535G of the sensor area 540 designed as shown in FIG. 8 are formed in the same layer.

Accordingly, the source electrode, the drain electrode, and the gate electrodes 535S, 535D, and 535G are all formed in the same layer and formed in one process.

For example, the source electrode, the drain electrode, and the gate electrode 535S, 535D, and 535G can be respectively formed by forming an electrode layer and simultaneously patterning a corresponding electrode layer.

Thus, a process step can be reduced, and a process time and cost can be reduced by simultaneously forming three electrodes 535S, 535D, and 535G that do not overlap each other.

The metal layer can be formed of at least one of Ni, Zn, Pd, Ag, Cd, Pt, Ga, In, and Au, but is not limited thereto.

A passivation layer 536 is formed on the electrodes 535S, 535D, and 535G.

The passivation layer 536 is formed on the entire sensor chip 500 to protect the sensor area 540 and the electrodes 535S, 535D, and 535G.

The passivation layer 536 can be formed of a material resistant to moisture, and can be formed of, for example, an oxide layer, a nitride layer, or a carbide layer.

In addition, the passivation layer 536 can be applied with a polymer resin, but is not limited thereto.

The passivation layer 536 exposes only the upper portion 551 of the plurality of channel areas 550, the gate electrode 540, and the plurality of pads 511 in the sensor chip 500, and covers all other areas.

Accordingly, the area exposed by the passivation layer 536 is very limited.

In particular, in the sensor area 540, only the gate electrode 535G and the channel area 550 are exposed to induce a reaction by directly contacting the specimen.

In the pad area 510, each pad 511S, 511D, 511G is exposed in an insulated state, and electrically in contact with each pad 158 of the circuit board 150 through a connecting member through an upper connecting member 140.

Figure 14A:
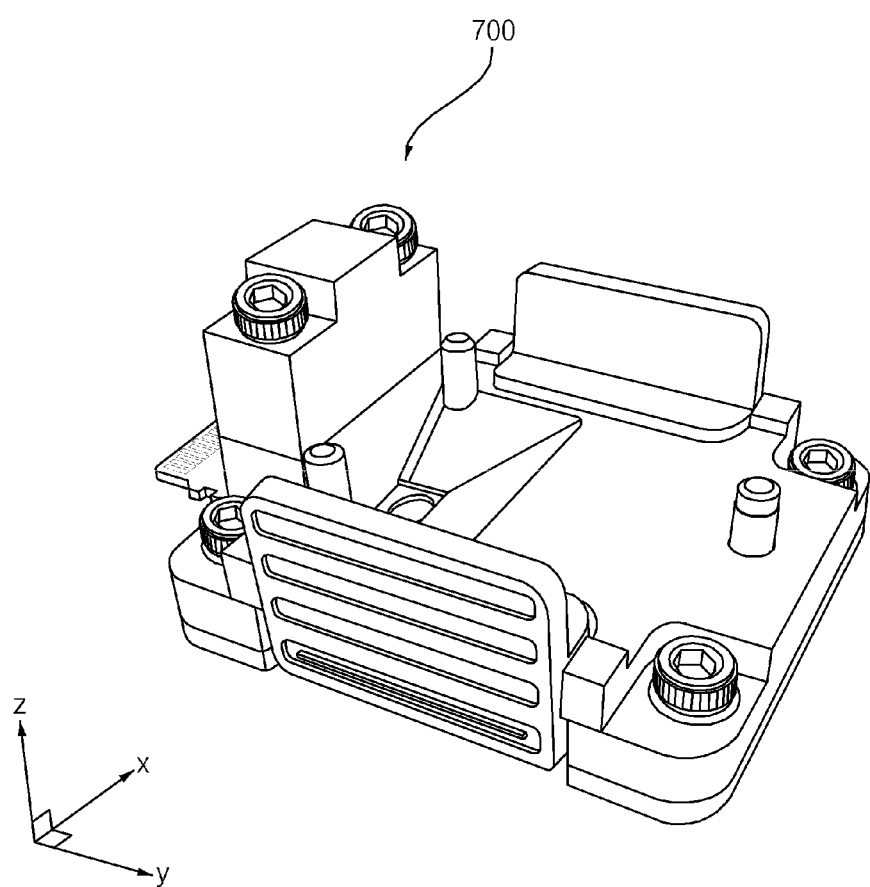
FIGS. 14A and 14B are respectively a perspective view and a top view of a probe device for error checking of a biosensor chip.

As shown in FIG. 14A, probe material 610 is attached to each of the channel areas 550 and is exposed as described above to activate the sensor.

The probe material 610 is a material that reacts specifically to a target material to be detected by the sensor. When the target material is an antigen, an antibody can be attached thereto, or when the target material is an antibody, an antigen can be attached thereto.

When the channel 533 is formed of graphene, a linker material (not shown) can be attached for smooth connection between the probe material 610 and graphene, and a process of attaching the probe material 610 after attaching a linker material on graphene is defined as an activation process.

The linker material is different depending on the material constituting the channel 533 and the probe material 610, and in the case of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphtharate, polycarbonate, and combinations thereof.

In addition, the linker material can be formed of a combination of polyurethane and NOA (e.g. NOA 68). However, the linker material is not limited thereto, and can be made of various polymers having flexibility.

An electrical detection signal according to a reaction of the sensor chip 500 can be described with reference to FIGS. 10A and 10B.

When the target material does not exist in the specimen as shown in FIG. 10A, the source electrode 535S receives a source voltage and the gate electrode 535G receives a gate voltage by the voltage applied to each pad 511.

The gate electrode 535G is exposed to the accommodating portion 119 and comes into contact with the specimen provided from the outside to apply a bias voltage to the specimen. Therefore, the specimen exists in a state of being partially charged with At this time, the drain current Ids (e.g., in ampere) read from the drain electrode 535D is as shown in FIG. 11.

That is, when there is no target material reacting with the probe material 610 in the specimen 600, the drain current Ids has a first value I1, which is defined as a reference current.

Figure 14B:
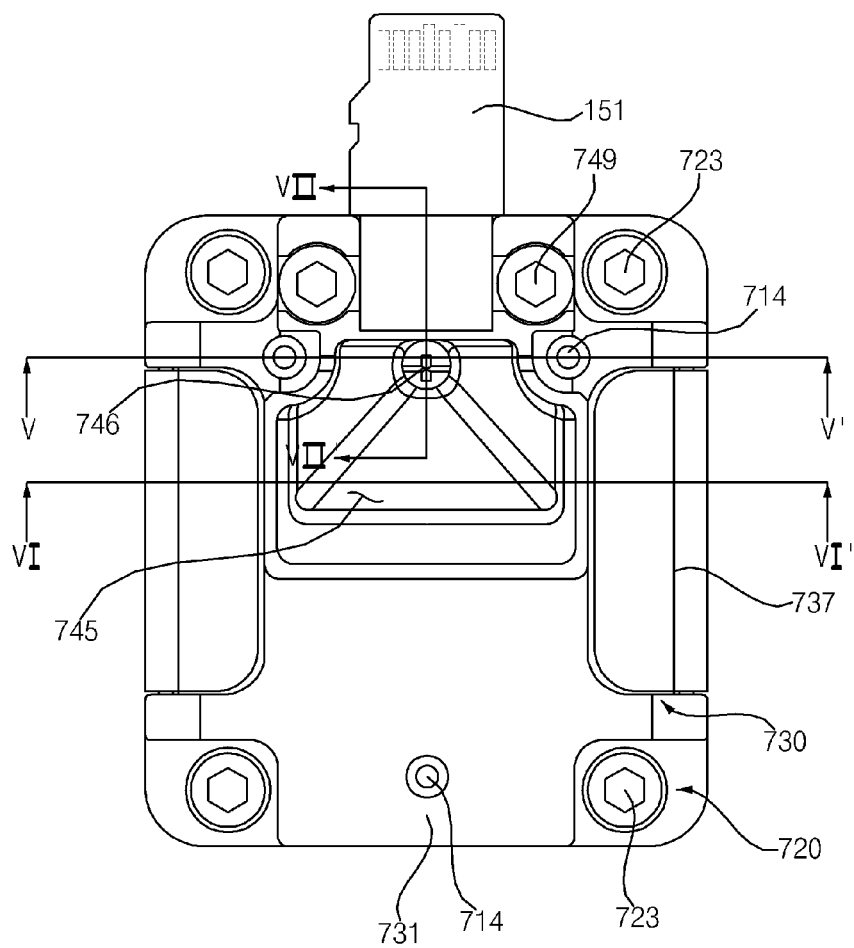

At this time, as shown in FIG. 14B, when the target material 650 exists in the specimen 600, the channel 533 is charged with a specific carrier as the target material 650 reacts with the probe material 610. For example, as shown in FIG. 14B, a depletion state in which charges are accumulated in the channel 533 can proceed.

Figure 15:
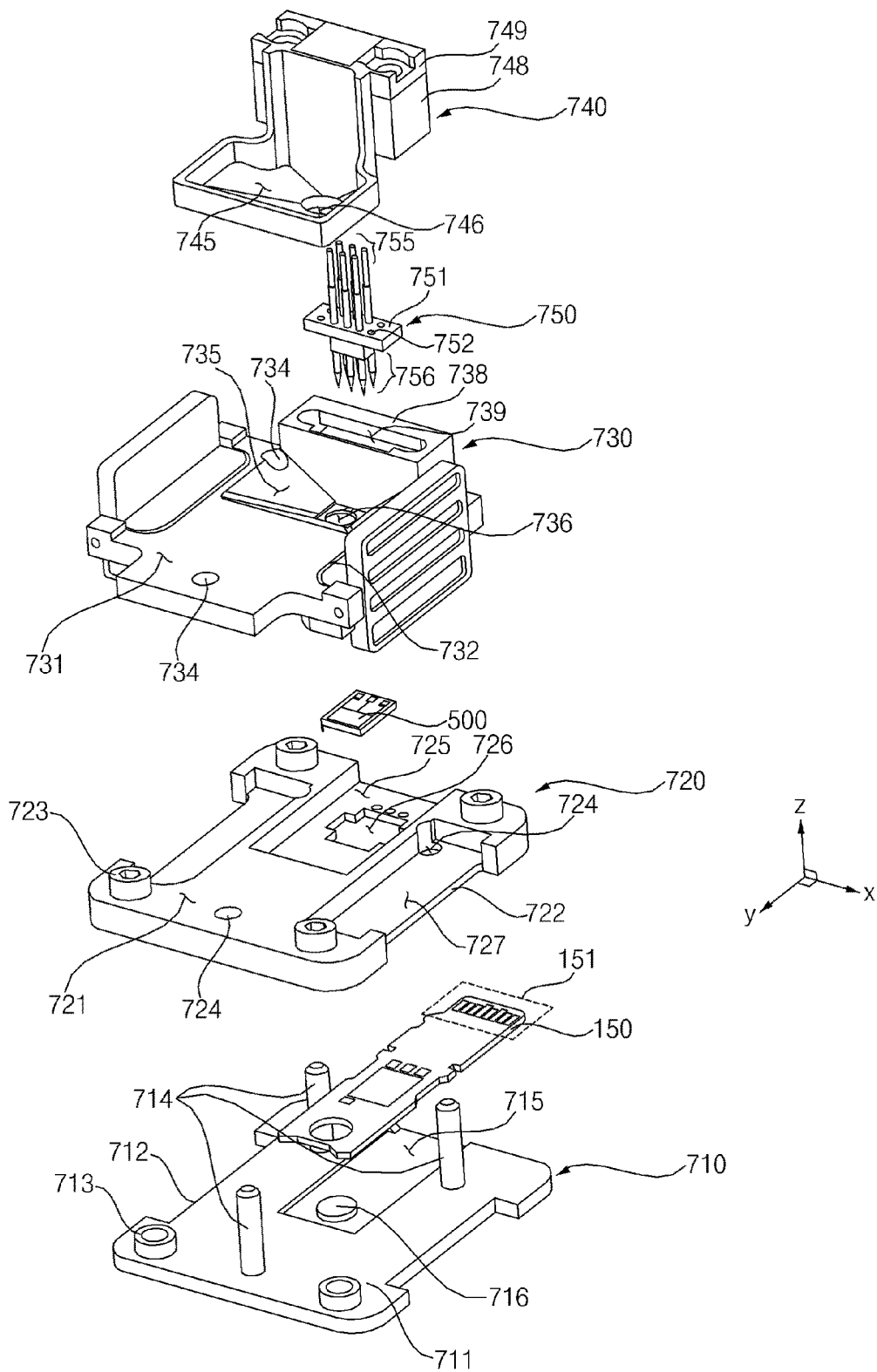
FIG. 15 is an exploded perspective view illustrating an example of the probe device of FIGS. 14A and 14B.

Accordingly, as the drain current Ids read from the drain electrode 535D increases, it has a second value I2 of FIG. 15.

At this time, the amount of accumulated charge is proportional to the area of the channel 533. Thus, when the number of channel 533 is one, the drain current Ids has a second value I2. When the number of channels 533 is two or more, the drain current Ids has a third value I3 greater than the second value I2. When the number of channels 533 is three or more, the drain current Ids has a fourth value I4 greater than the third value I2. Accordingly, the value of the drain current Ids read from the drain electrode 535D is amplified.

At this time, even when one channel 533 does not operate as the plurality of channels 533 are spaced apart from each other, the existence of the target material can be recognized by causing the drain current Ids to increase or decrease in another channel 533.

As described above, the graphene channel sensor chip 500 has a multi-channel structure having a plurality of channels spaced apart from each other, thereby amplifying a drain current and compensating for a malfunctioning channel.

In such a sensor chip 500, both the gate electrode 535G and the channel area 550 can be exposed by the distal end opening of the accommodating portion 119 having a circle larger than the circumference of the gate electrode 535G.

In addition, the plurality of channel areas 550 are formed to be spaced apart at the same angle and at the same distance from the center O of the sensor area 540 opened by the accommodating portion 119 such that the specimen is uniformly contacted, and formed in a shape surrounding the source and drain electrodes 535S and 535D in order to dispose the channel 533 between the source and drain electrodes 535S and 535D, thereby optimizing a structure.

In FIG. 8, each electrode connection portion 521 connected from one end of each electrode 535S, 535D, 535G to the pad 511 is included, and each electrode connection portion 521 is formed of the same metal layer as the electrode 535S, 535D, 535G and thus does not overlap.

In FIG. 8, it is illustrated that the pads 511 is formed in a line at one end of the sensor chip 500, but aspects of the present disclosure are not limited thereto.

chip 500 can be variously changed as long as the transistor in which the gate electrode 535G and the plurality of channels 533 are exposed is maintained in the accommodating portion 119.

Accordingly, the position of the pad 511 can also be variously changed. However, the positions of the connecting member 140 and the connection pad 158 of the circuit board 150 are also changed according to the change in the position of the pad 511.

Meanwhile, the sensor chip 500 including the plurality of channels 533 spaced apart from each other can be designed to detect different target materials.

Hereinafter, a method of manufacturing a graphene-based multi-channel sensor chip 500 of the present specification will be described with reference to FIG. 12.

Figure 12:
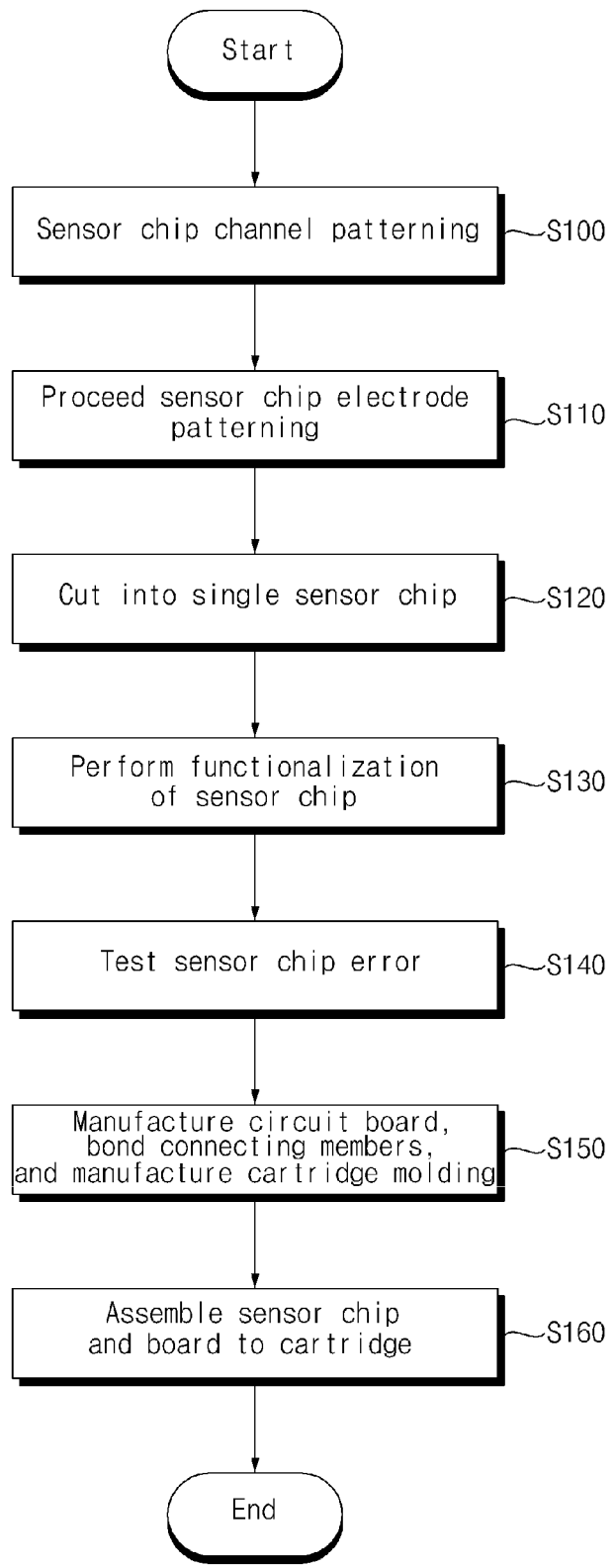
FIG. 12 is a flowchart illustrating a manufacturing process of the biosensor cartridge of FIG. 5.

Referring to FIG. 12, firstly, patterning of the sensor chip 500 for manufacturing the sensor chip 500 is performed on a semiconductor wafer (S100).

The manufacturing of the sensor chip 500 is a process for manufacturing the sensor chip 500 of FIGS. 8 to 9, and an insulating layer 532 made of oxide or nitride is formed on the semiconductor substrate 530.

When the semiconductor substrate 530 is a silicon substrate, the insulating layer 532 can be formed of silicon oxide or silicon nitride, and can be formed by various methods. For example, a silicon oxide layer can be formed on the surface through heat treatment.

A plurality of channels 533 are formed on the insulating layer 532 to be spaced apart from each other.

to simultaneously manufacture a plurality of unit sensor chips 500, and can perform channel patterning for manufacturing the plurality of unit sensor chips 500.

A channel layer is patterned with a plurality of channels 550 designed for each unit sensor chip 500 (S100).

For example, when the plurality of channels 550 are formed of graphene, graphene is stacked on the insulating layer and then graphene is patterned to form a plurality of channels 550 spaced apart from each other in the area of the unit sensor chip 500.

Next, electrode patterning for forming electrode and pad as shown in FIGS. 10 to 18 is performed (S110). At least one metal layer among Ni, Zn, Pd, Ag, Cd, Pt, Ga, In, and Au for forming the electrode 535S, 535D, 535G is stacked, and the metal layer is patterned to simultaneously form the source electrode, the drain electrode, and the gate electrode 535S, 535D, 535G, the pad 511 connected to each electrode, and the connection portion 521 for connecting them. The passivation layer 536 is formed on the electrode 535S, 535D, and 535G, and patterning is performed to expose only the plurality of channel areas 550, the gate electrode 540, and the plurality of pads 511 (511S, 511D, 511G).

When a plurality of unit sensor chips 500 are generated on one semiconductor wafer as described above, a cutting process of cutting the plurality of unit sensor chips 500 into a single sensor chip 500 (e.g., individual sensor chips 500) is performed (S120).

The cutting process can be performed by laser scribing, or laser scribing can be performed together with a physical cutting process.

A single sensor chip 500 cut into a unit sensor chip 500 is defined as the sensor chip 500 of FIG. 10, and functionalization of the sensor chip 500 is performed (S130).

The functionalization of the sensor chip 500 is defined as a process of attaching probe material that performs a specific reaction to a target material to be detected by each sensor to an exposed channel area of each sensor chip 500.

For the functionalization of the sensor chip 500, when the channel 533 is formed of graphene, a linker material can be attached for a smooth connection between the probe material 610 and graphene, a process of attaching the probe material 610 after attaching the linker material on the graphene is performed.

The linker material is different depending on the material constituting the channel 533 and the probe material 610, and in the case of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphtharate, polycarbonate, and combinations thereof.

In addition, the linker material can be formed of a combination of polyurethane and NOA (e.g. NOA 68). However, the linker material is not limited thereto, and can be made of various polymers having flexibility.

When the functionalization of the sensor chip 500 is completed, a test process of the sensor chip 500 is performed (S140).

Such error checking of the sensor chip 500 is performed using a probe device according to an embodiment as a medium.

That is, a performance test can be performed on the sensor chip 500 in a manner in which the circuit board 150 of the manufactured cartridge 100 and the sensor chip 500 are respectively placed in a probe device 700 and electrically connected thereto using a probe pin and then a connection pad 158 of the circuit board 150 is inserted into a reader part of a test device.

The performance test of the sensor chip 500 will be described in detail later with reference to FIG. 13.

As such, it is possible to simultaneously perform a physical test as to whether patterning has been performed accurately according to the design and a functional test as to whether electrical connection is made.

In addition, the basic resistance value of each sensor chip 500 is received, and a failure can be determined according to whether a corresponding basic resistance value is within a certain range.

When such an error check is finished, the failure sensor chip is classified and only the sensor chip 500 that passed the check can be used as a valid chip.

Meanwhile, the circuit board 150 can be manufactured through a separate process. As described above, in the circuit board 150, a base member, which is the base material of the circuit board 150, is cut and punched according to the design of the circuit board 150, and a circuit pattern is formed in one side of the base member to complete the circuit board 150.

In this case, one side of the circuit board 150 is disposed as a rear surface, and the connection pad 158, which is a part of the circuit pattern, is exposed on the rear surface.

The connecting members 140 are respectively attached to the exposed connection pad 158 according to a preset number (S150).

The bonding of the pad 158 and a first surface of the connecting member 140 can be performed by soldering so as to simultaneously satisfy the electrical and physical attachment. Accordingly, a second surface of the connecting member 140 is maintained as a free end.

Meanwhile, the upper housing 110 and the lower housing 120 can be manufactured through separate processes.

Separate molds can be manufactured respectively for the upper housing 110 and the lower housing 120 to perform a molding process. As such, when a resin material, such as polycarbonate, is injected into a mold and then the mold is removed in a vertical direction, the upper housing 110 is manufactured.

Next, in a state in which the sensor chip 500 is disposed in the area of the sensor chip 500 of the lower housing 120 of the cartridge 100 and the circuit board 150 is placed thereon, the upper housing 110 is pressed, so that a second surface 145 of the connecting member 140 is fixed in a state of being bonded to the pad 511 of the sensor chip 500 (S160).

Accordingly, electrical connection and physical connection between the circuit board 150 and the sensor chip 500 are simultaneously achieved.

In this state, by ultrasonically welding the end of the lower housing 120 and the ends of the side surfaces of the upper housing 110 of the cartridge 100 to induce melting of some resin and harden the melted resin, the cartridge 100 is integrated. The manufacturing of the cartridge 100 is completed in a state in which the upper housing 110 and the lower housing 120 cannot be separated due to the fusion.

Through such a manufacturing process, failure of the sensor chip 500 is firstly filtered and then assembling is performed. In the assembling step, a high-temperature process by wire bonding is not applied, so that the functionalized sensor chip 500 is prevented from being deteriorated due to heat.

In addition, since a process for protecting a device by performing plastic molding is not added after wire bonding of the sensor chip 500, deterioration of the probe material of the sensor chip 500 due to high temperature is prevented.

The biosensor cartridge 100 accommodating the graphene-based multi-channel sensor chip 500 manufactured as described above performs an inspection step for error filtering of a sensor chip as follows.

Figure 13:
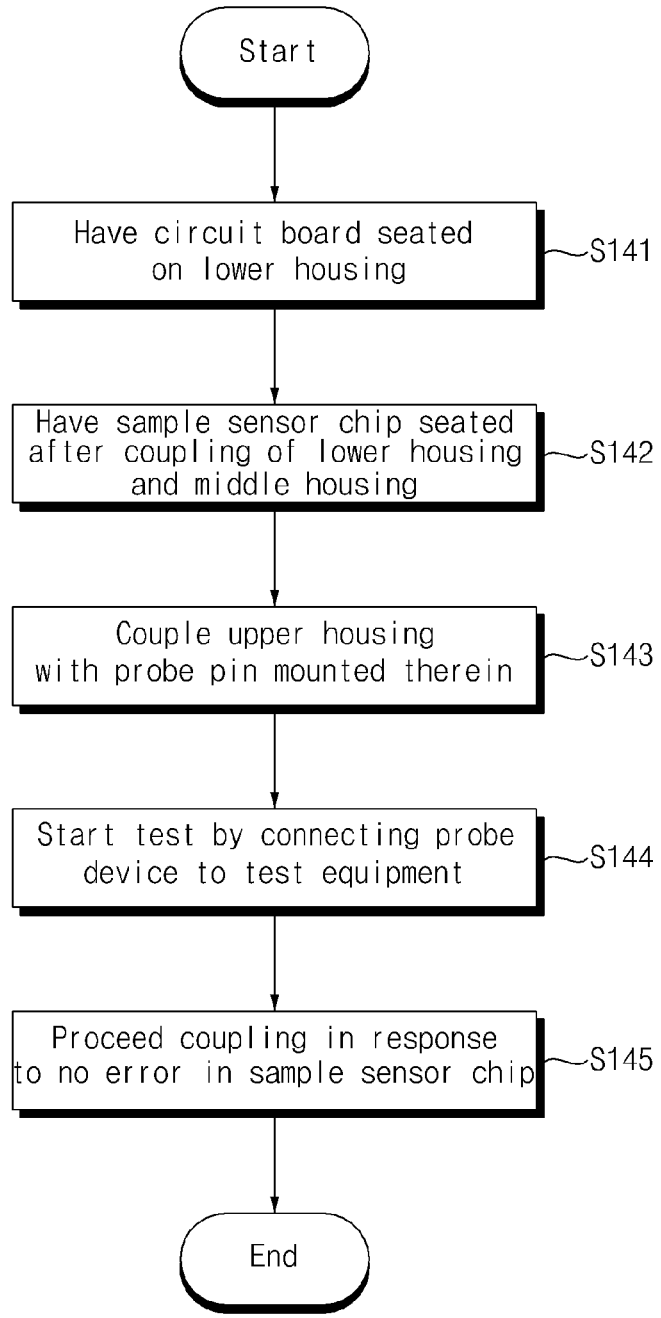
FIG. 13 is a flowchart illustrating an error check process of a biosensor chip during the manufacturing process of FIG. 12.

FIG. 13 is a flowchart illustrating an error check process of a biosensor chip during the manufacturing process of FIG. 12, FIGS. 14A and 14B are a perspective view and a top view of a probe device for error checking of a biosensor chip, and FIG. 15 is an exploded perspective view illustrating an example of the probe device of FIGS. 14A and 14B.

Referring to FIGS. 14A to 15, a probe device 700 for error checking of the biosensor chip 500 is provided.

In the probe device 700, one of diced sensor chips 500, for example, a sample sensor chip 500, is mounted, one of circuit boards 150 disposed in the cartridge 100 is mounted, and then a probe pin(s) 756 is aligned to connect the sensor chip 500 and the connection pad 158 of the circuit board 150 to each other.

As such, in a state in which the circuit board 150 and the sensor chip 500 are electrically connected to each other by the probe pin(s) 756 in the probe device 700, a connection terminal 153 of the circuit board 150 is inserted into the test device to thereby provide a reference voltage to each pad 511 of the sensor chip 500 and read an output current through the connection terminal 153 of the circuit board 150.

In doing so, it is possible to read a base resistance value of the sensor chip 500 and detect a change in a drain current caused by a source voltage to determine whether the sensor chip 500 is operating.

When the operation of the sensor chip 500 is confirmed by the above-described inspection, the sensor chip 500 is classified as a valid sensor chip 500 and the cartridge 100 is assembled.

The error checking of the sensor chip 500 using the probe device 700 is performed without physical coupling between the sensor chip 500 and the circuit board 150, so there is no damage to each element. In addition, the error check is performed in the same manner as a diagnosis through the previously manufactured circuit board 150, without a need for manufacturing a separate circuit board 150, thereby reducing a manufacturing cost.

Specifically, the probe device 700 of the embodiment will be described with reference to FIGS. 14A to 24.

The probe device 700 includes a lower housing 710, a middle housing 720, an upper housing 730, and an upper cover 740, as shown in FIGS. 14A to 15.

The lower housing 710 can include a body portion 711 in contact with the middle housing 720, and a recessed portion 715 recessed from the body portion 711 in a downward direction (z-direction). In the recessed portion 715, the circuit board 150 can be mounted with the connection pad 158 being exposed to the outside.

The middle housing 720 can be disposed on an upper surface of the body portion 711 of the lower housing 710.

The middle housing 720 can include a middle body portion 721 overlapping with the body portion of the lower housing 710, and a middle recessed portion 725 (e.g., middle depression) recessed from the middle body portion 721 in the downward direction (z direction).

A chip area 726 for accommodating the sensor chip 500 is defined in a bottom surface of the middle recessed portion 725. The chip area 726 can be formed as a chip opening having an area smaller than the chip area as shown in FIG. 15, but the chip area 726 can also be implemented as a fixing protrusion capable of fixing the sensor chip 500.

The upper housing 730 includes an upper body 731 on the middle body 721 to cover the middle housing 720, and the upper body 731 includes an upper recessed portion 735 that exposes the sensor area 540 of the sensor chip 500 positioned therebelow.

A probe pin guide 738 extending in the recessed portion 735 of the upper housing 730 and protruding upward is formed.

The probe pin guide 738 includes a hole 739 having a step so that a probe pin module 750 can be inserted, and the probe pin guide 738 guides the probe pin(s) 756 to connect the probe pin module 750 to the lower sensor chip 500 pad 511 and the circuit board 150 to the pad(s) 158.

The upper cover 740 is disposed on an upper surface of the upper housing 730.

The upper cover 740 covers the probe pin module 750 and has a structure for protecting the probe pin module 750 from the outside. The upper cover 740 includes a cover guide 748 for covering the probe pin guide 738, and an accommodating portion 745 extending from a lower portion of the cover guide 748 and covering the upper recessed portion 735 of the upper housing 730.

The accommodating portion 745 is implemented in a concave shape in which a predetermined specimen can be accommodated, and an opening 746 for exposing the sensor area of the sensor chip 500 is formed at the bottom of the accommodating portion 745.

As described above, by combining the plurality of modules in a state where the sensor chip 500 to be tested and the circuit board 150 are arranged, one probe device 700 is formed.

The lower housing 710 and the middle housing 720 can be coupled through a plurality of bonding materials (e.g., via adhesive bonding). For example, as shown in FIG. 15, a screw hole 713, 723 is formed in each corner (at two corners), one screw hole 713 of the lower housing 710 and one screw hole 723 of the middle housing 720 overlap each other to form a common screw hole 713, 723, and a single screw member is coupled to the screw hole 713, 723 to simultaneously couple the lower housing 710 and the middle housing 720.

Alternatively, the lower housing 710 and the middle housing 720 can be fitted so that the screw holes 713 and 723 can overlap each other (e.g., in the Z direction, which can be a vertical direction or top-down direction).

In this case, the upper surface of the body portion 711 of the lower housing 710 can further include at least one coupling protrusion 714 protruding in an upward direction (Z direction).

The coupling protrusion 714 can be provided as at least three as shown in FIG. 15, and can have a greater number than three. The coupling protrusions 714 can be spaced apart from one another and two of the coupling protrusions 714 disposed at a first end (e.g., rear end) of the lower housing 710 can be symmetrically disposed about a third coupling protrusion 714 disposed at a second end (e.g., front end) of the lower housing 710.

The coupling protrusion 714 can include one coupling protrusion 714 disposed on a front side (e.g. front end) of the upper surface of the body portion 711 and two coupling protrusions 714 disposed on a rear side (e.g., rear end) of the upper surface of the body portion 711. The two coupling protrusions 714 disposed on the rear side can be formed on both sides of the bottom recessed portion 715.

When the three coupling protrusion 714 are formed, the front coupling protrusions 714 can be disposed at a center of a distance between the rear coupling protrusions 714.

Therefore, when the three coupling protrusions 714 are coupled to the upper housing 730, a force is uniformly applied thereto, so that the coupled state can be maintained without distortion.

In addition, a coupling hook 737 is disposed on both sides (e.g., opposing sides) of the upper housing 730 for coupling with the middle housing 720 and the lower housing 710 from the upper housing 730.

The coupling hook 737 is rotatably coupled to a shaft in a side surface of the body portion of the upper housing 730, and can cover and fix the side surface of the body portion of the lower housing 710 by rotation with respect to the shaft.

In addition, the upper housing 730 and the upper cover 740 include a coupling hole 749 on an upper surface of the cover guide 748 of the upper cover 740, and the upper housing 730 and the upper cover 740 can be coupled using a screw member that simultaneously couple the coupling hole 749 and a coupling hole 739 of the probe pin guide 738 of the upper housing.

Hereinafter, each configuration will be described in detail with reference to the drawings.

Figure 16:
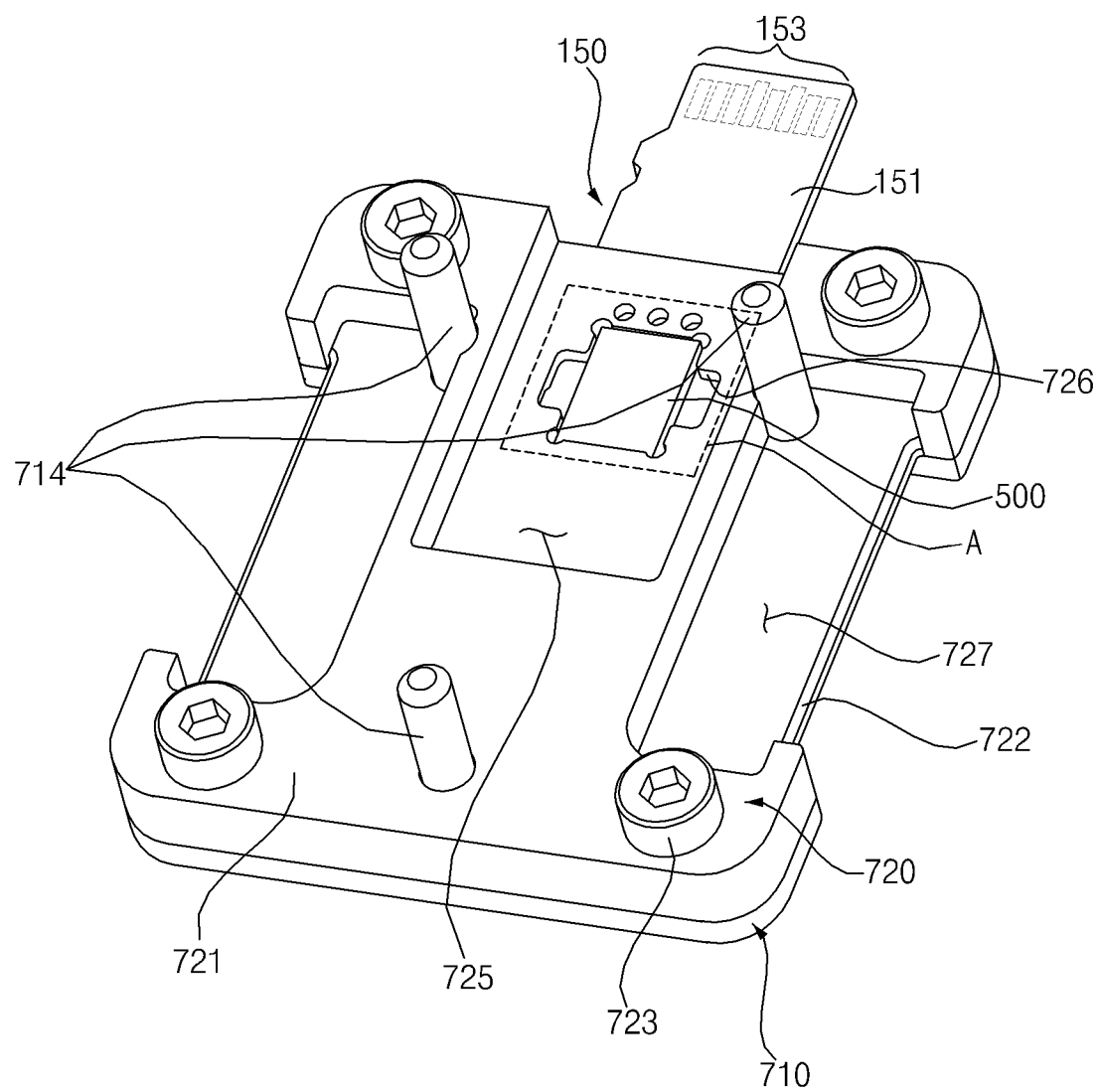
FIG. 16 is a detailed view of a lower housing of the probe device of FIG. 15.
Figure 17:
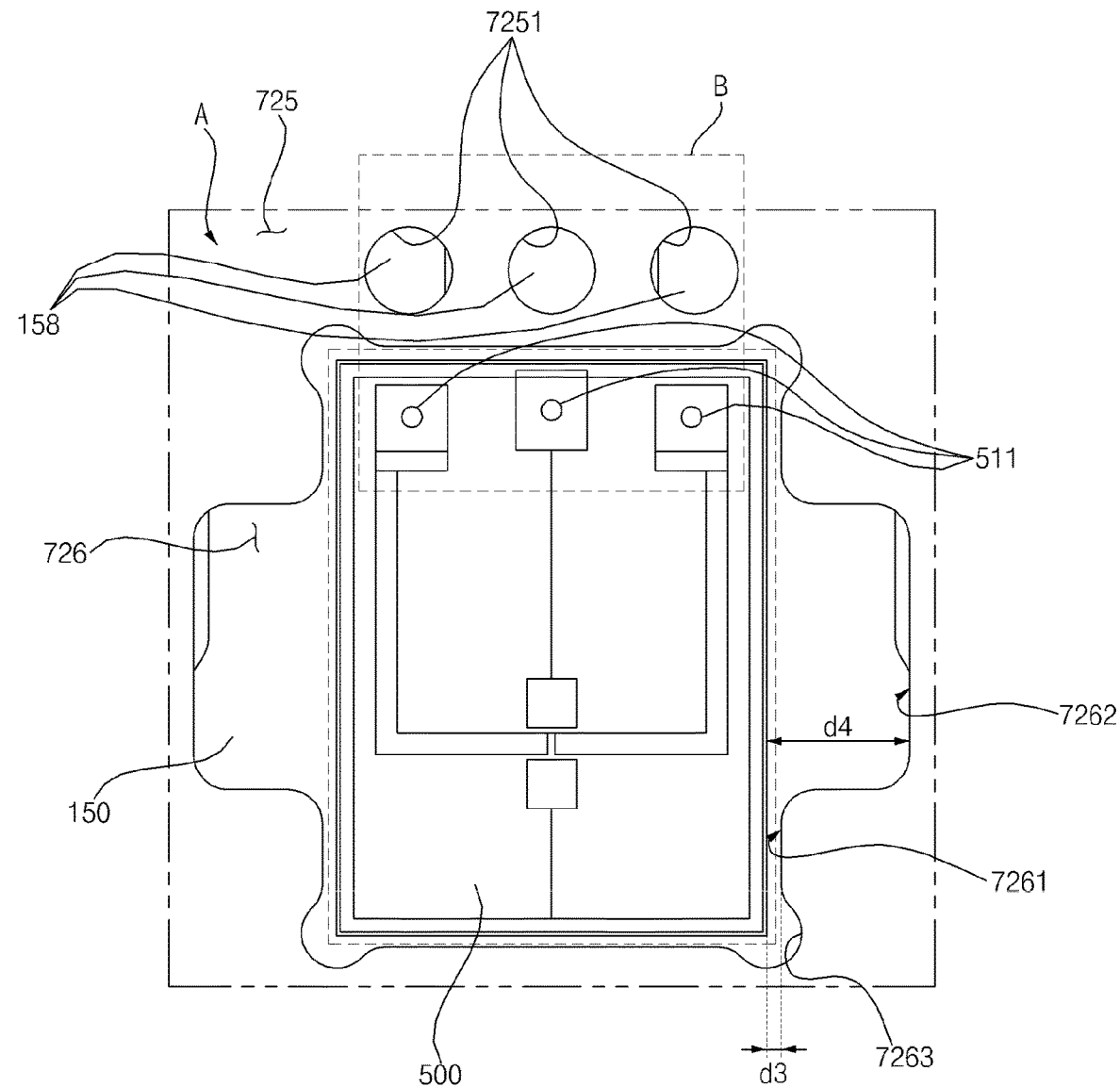
FIG. 17 is an enlarged view of area A of FIG. 16.

FIG. 16 is a detailed view of the lower housing 710 of the probe device 700 of FIG. 15, and FIG. 17 is an enlarged view of area A of FIG. 16.

First, as shown in FIG. 15, in the lower housing 710, the body portion 711 defining an entire area of the probe device 700 is formed.

The body portion 711 is a planar structure extending in the x-axis and y-axis directions, and can have, for example, a quadrangle shape as shown in FIG. 15.

In this case, a screw hole 713 for coupling with the upper middle housing 720 can be formed in each corner area of the quadrangle.

The screw hole 713 can be formed to protrude in an upward direction (z direction) from each corner area, and the protruding screw hole 713 can be coupled to a screw member in a state of being fitted with and coupled to the screw hole 723 of the upper middle housing 720.

A side surface 712 formed along the y-axis among side surfaces between the corner areas can be recessed so as to have a step in a direction toward the center.

The stepped side surface 712 can be defined as a hook coupling area for coupling with the hook 737 of the upper housing 730.

In this case, a recessed portion 715 recessed from the body portion 711 in a downward direction (z-direction) can be formed to be stepped to a predetermined depth from the upper surface of the body portion 711, and the depth of the step can be equal to a width of the circuit board 150.

A width of the recessed portion 715 can also be the same as the width of the circuit board 150, however, the recessed portion 715 can have a different width from the circuit board 150.

In this case, a board protrusion 716 can be formed to protrude from a bottom surface of the recessed portion 715 so as to be coupled to a coupling hole of the circuit board 150. The board protrusion 716 can be in the form of a circular protrusion.

The board protrusion 716 has a height equal to or lower than a height of the upper surface of the body 711, thereby not protruding upward from the upper surface of the body 711.

When the coupling hole of the circuit board 150 and the board protrusion 716 are fitted and coupled, a side wall is not formed because a rear side of the recessed portion 715 is exposed to the outside so that the connection terminal 153 of the circuit board 150 is exposed to the outside.

Therefore, when the middle housing 720 and the lower housing 710 are coupled to each other in a state in which the circuit board 150 is coupled on the lower housing 710, the connection terminal 153 of the circuit board 150 is exposed to the outside through the open rear side of the recessed portion 715.

A plurality of coupling protrusions 714 protrudes from the upper surface of the body portion 711 of the lower housing 710 in an upward direction (Z direction).

The coupling protrusions 714 can include one coupling protrusion 714 disposed on the front side of the upper surface of the body 711 and two coupling protrusions 714 disposed on the back side of the upper surface of the body portion 711, and the two protrusions 714 disposed on the rear side can be formed on both sides of the bottom recessed portion 715.

When the three coupling protrusions 714 are formed, the front coupling protrusions 714 can be disposed at a center of a distance between the rear coupling protrusions 714.

The respective coupling protrusions 714 can have the same height, and when coupled to the upper housing 730, the respective coupling protrusions 714 can each have a sufficient depth to pass through the coupling hole 734 so that each coupling protrusion 714 is partially exposed to the outside.

That is, each coupling protrusion 714 has a height greater than the sum of the thicknesses of the middle housing 720 and the thickness of the upper housing 730.

When the three coupling protrusions 714 are coupled to the upper housing 730, a force is uniformly applied, so that the coupled state can be maintained without distortion.

Meanwhile, referring to FIGS. 16 and 17, the middle housing 720 is disposed on the lower housing 710.

The middle body portion 721 of the middle housing 720 is disposed on the upper surface of the body portion of the lower housing 710.

The middle body portion 721 is a planar structure extending in the x-axis and y-axis directions, and has the same shape as the body portion 711 of the lower housing 710 positioned below.

The middle body 721 can have a quadrangle shape.

In this case, a screw hole 723 for coupling with the upper lower housing 710 can be formed at each corner area of the rectangle.

The screw hole 723 can be formed to protrude in an upward direction (z direction) at each corner area, and the protruding screw hole 723 can be coupled to a screw member in a state of being fitted with and coupled to the screw hole 713 of the lower housing 710 positioned below.

A side surface 722 formed along the y-axis among side surfaces between the respective corner areas can be recessed so as to have a step in a direction toward a center.

The stepped side surface 722 can be defined as a hook coupling area for coupling with the hook 737 of the upper housing 730.

It can be formed by being depressed from the upper surface of the middle body portion 721 to the center from the stepped side surface 722, but is not limited thereto.

The middle recessed part 725 recessed in the downward direction (z-direction) from the middle body portion 721 can be formed to be stepped from the upper surface of the body portion to a predetermined depth.

A chip area 726 for accommodating the sensor chip 500 is defined in a bottom surface of the middle recessed part 725. The chip area 726 can be formed as an open chip opening having an area smaller than the chip area as shown in FIG. 16, but can also be implemented as a fixing protrusion in a state in which the sensor chip 500 can be fixed.

A plurality of pin openings 7251 exposing the connection pad 158 of the lower circuit board 150 are formed on the bottom surface of the middle recessed part 725.

Referring to FIG. 17, the chip opening 726 is formed to have a width and length equal to or greater than that of the sensor chip 500 in the central area.

In this case, the separation distance d3 between the sensor chip 500 and the sidewall 7261 of the chip opening 726 can be formed to have 0.05 to 0.1 mm or less.

In addition, in the chip opening 726, each corner area 7263 in which the sensor chip 500 is disposed can be concavely formed to be more open toward the bottom surface of the middle recessed part 725 in a rounded chamfer shape.

In addition, each sidewall 7262 of the central area where the sensor chip 500 is disposed includes an extended opening area that is further opened toward the bottom surface of the middle recessed part 725.

The extended opening area can be formed to have a width d4 of 1 to 3 mm, and the extended opening area is equally formed on both sides of the central area where the sensor chip 500 is placed, so that the sensor disposed in the central area. When disposing or removing the chip 500, the sensor chip 500 can be lifted using tongs while minimizing physical impact such as forcibly holding or shaking.

The plurality of pin openings 7251 are formed in the chip openings (726) of the chip area 726 so as to be close to the pad(s) 511 of the sensor chip 500 of the sensor chip 500 disposed in the chip area 726 as shown in FIGS. 16 and 17. 726) is formed on one side.

At this time, when there are three pads 511(s) of the sensor chip 500, since three connection pads 158 of the circuit board 150 are also formed, the pin opening 7251 also connects each connection pad 158. It is formed in three pieces to be exposed, and their positions are also formed to be aligned with the connection pads 158 of the circuit board 150, respectively.

Each of the pin openings 7251 can be formed in a circular shape having a predetermined diameter as shown in FIG. 17, and can be formed to be spaced apart from each other by a predetermined distance.

The pin openings 7251 can function as guides for connecting the probe pins 756 to the pads 511 of the lower circuit board 150 through which the probe pins 756 are respectively penetrated.

Accordingly, the diameter of the pin opening 7251 can be larger than the diameter of the end of the probe pin(s) 756.

When the sensor chip 500 is disposed in the central area of the chip opening as shown in FIG. 17, it is placed on the lower circuit board 150, and the sensor chip 500 has a pad 511 area in the pin opening 7251.

Accordingly, the three pads 511 in the pad area of the sensor chip 500 can be arranged to form a matrix with the three pin openings 7251.

In this way, area B of FIG. 17 is defined as a probe area to which a probe pin(s) 756 described later is connected.

However, as the number and shape of the connection pads 158 of the circuit board 150 and the pads 511 of the sensor chip 500 vary, the shape of the pin opening 7251 is also variable.

That is, the shape and number of the pin openings 7251 are formed to correspond to the number and shape of the connection pads 158 of the circuit board 150.

The middle body portion 721 includes a coupling hole 724 through which the coupling protrusion 714 of the lower housing 710 passes in the upper and side recessed parts 727. The coupling hole 724 can be formed in three to correspond to the number and shape of the coupling protrusion 714, at this time, the two coupling holes 724 formed on the rear side are the special wall of the side recessed part 727, That is, the step difference can be formed along the wall.

Figure 18A:
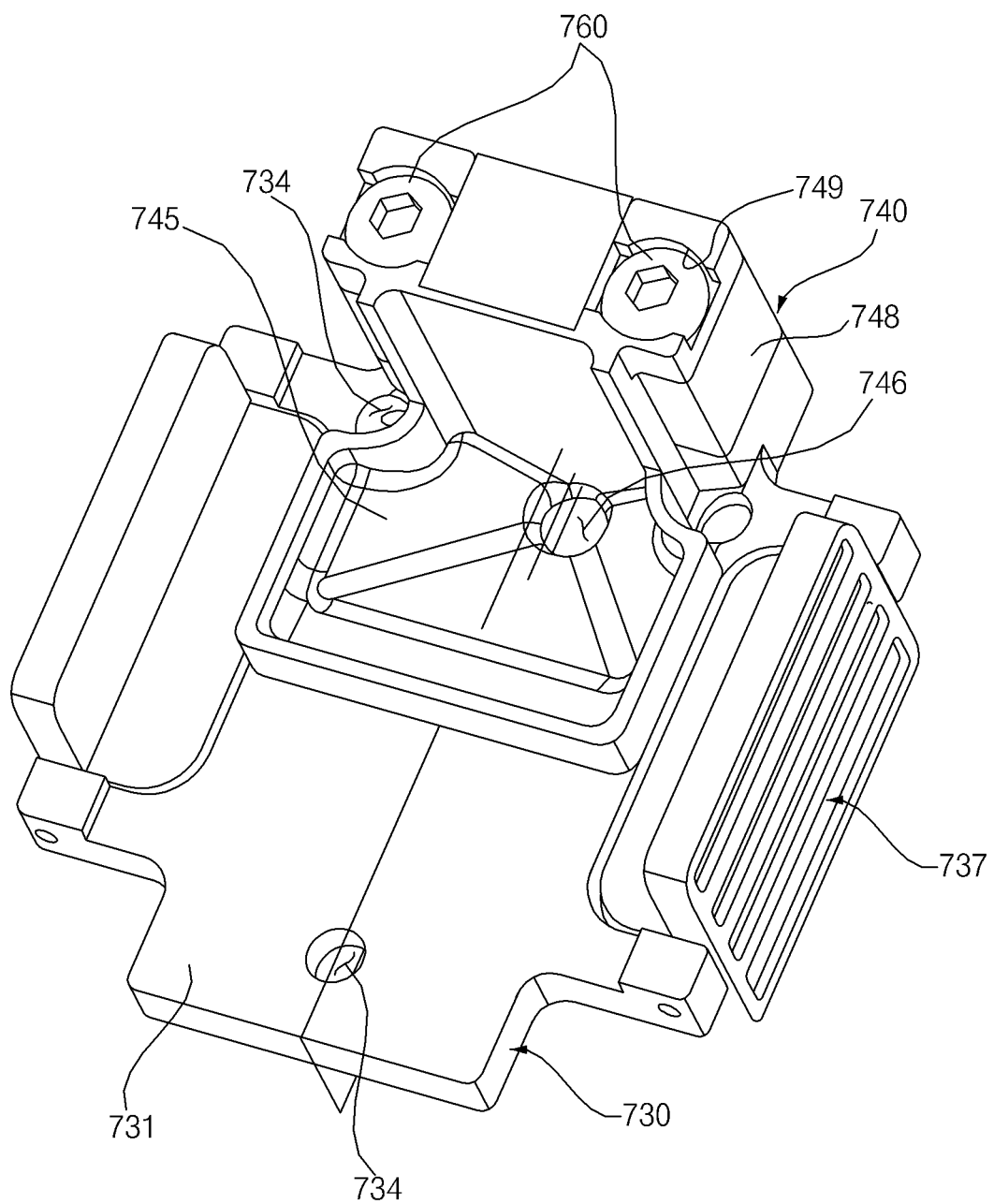
FIGS. 18A and 18B are respectively a top perspective view and a rear view of an upper housing of the probe device of FIG. 15.
Figure 18B:
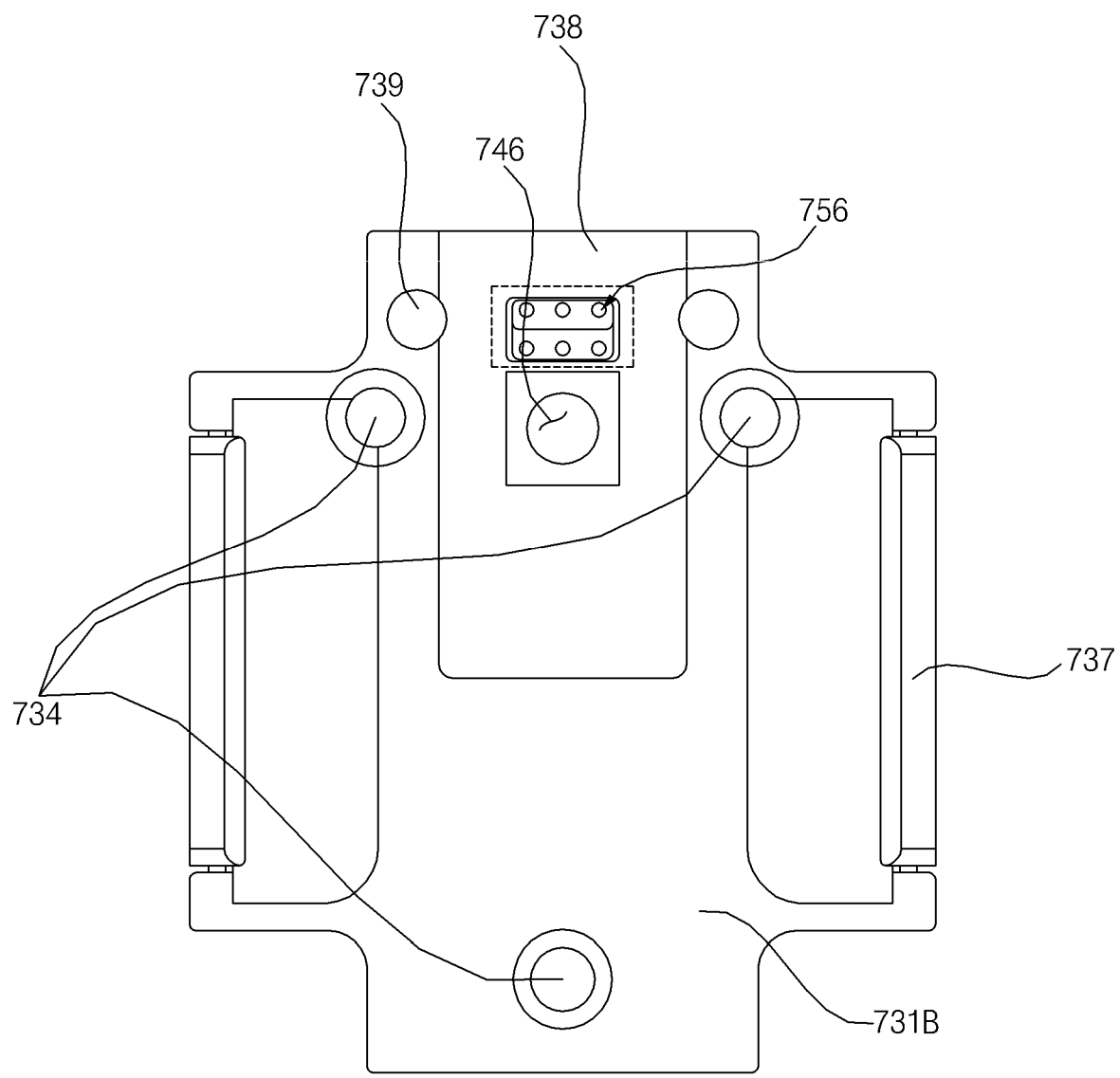

Meanwhile, the upper housing 730 is as shown in FIGS. 15 and 18A and 18B.

Figure 19:
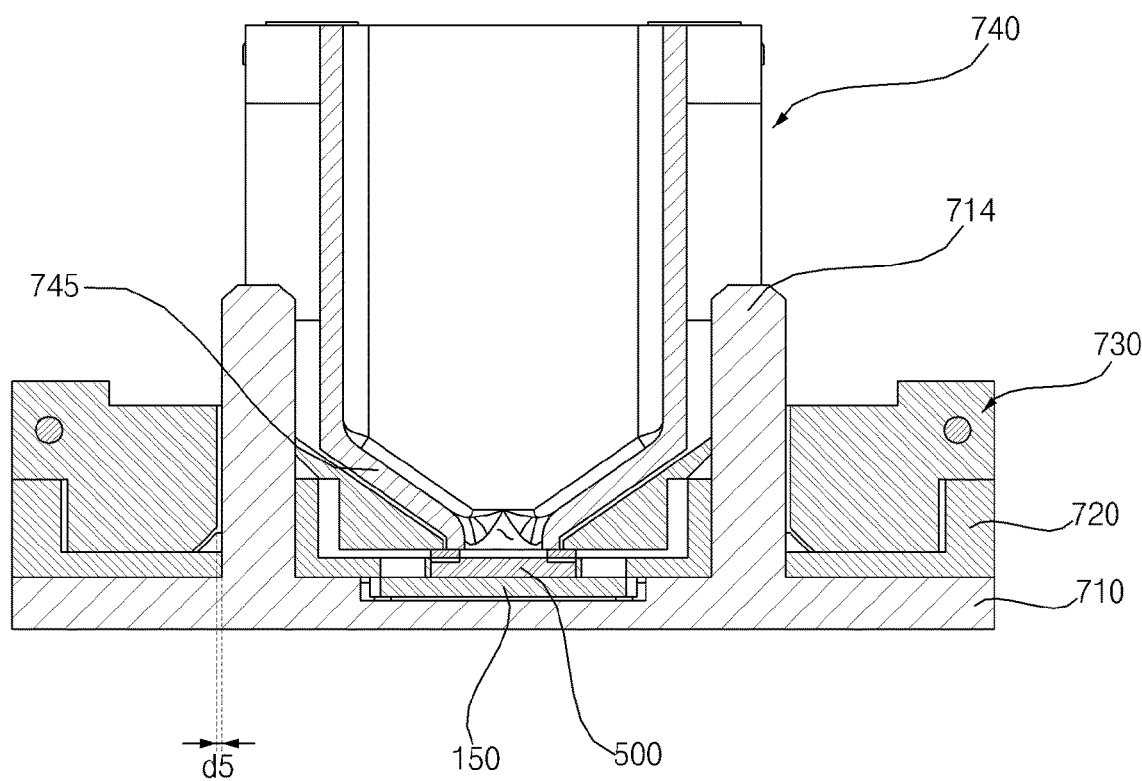
FIG. 19 is a cross-sectional view taken along the line V-V' of the probe device of FIG. 14B.

FIGS. 18A and 18B are a top perspective view and a rear view of the upper cover 740 of the probe device 700 of FIG. 15, and FIG. 19 is a cross-sectional view of the probe device 700 of FIG. 14B taken along the line V-V'.

Referring to FIGS. 15 and 18A and 18B, the upper housing 730 includes an upper body portion 731 on the middle body portion 721 to cover the middle housing 720, and the upper body portion 731 includes an upper recessed portion 735 that exposes the sensor area 540 of the lower sensor chip 500.

The upper body portion 731 is a planar structure extending in the x-axis and y-axis directions, and has a shape similar to that of the body portion 711 of the lower housing 710 below.

The upper body portion 731 has a rectangular shape, and the corner area is recessed into the center to open the screw hole 723 of the lower middle body portion 721.

The coupling hook 737 for coupling with the middle housing 720 and the lower housing 710 is formed in the side surfaces of the upper body 731.

Figure 20:
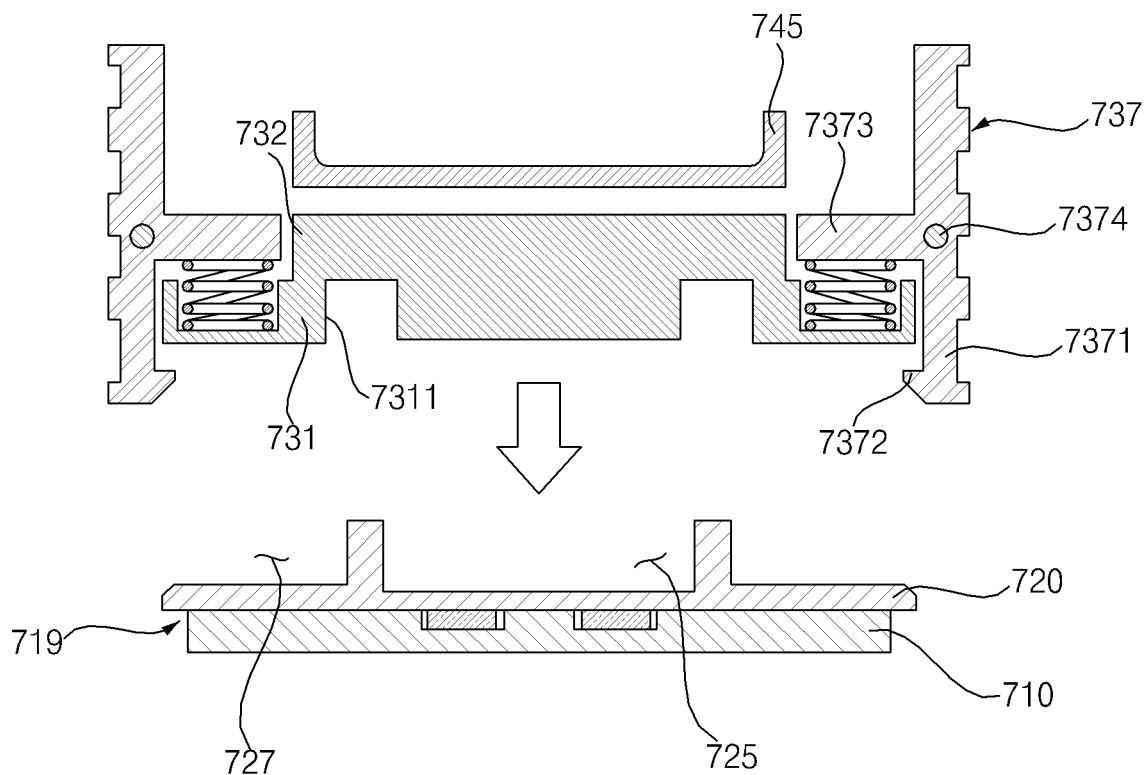
FIG. 20 is an exploded cross-sectional view of the probe device of FIG. 14B taken along the line VI-VI'.
Figure 21:
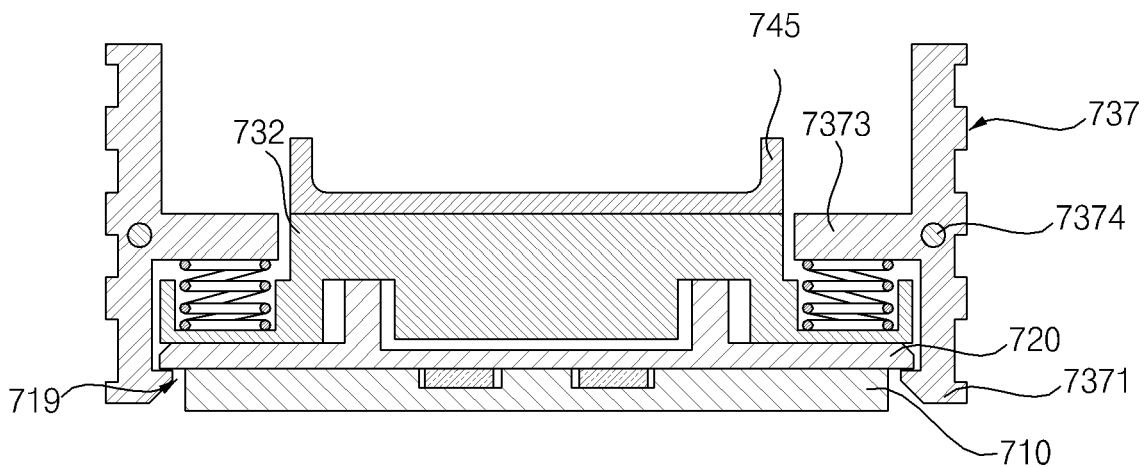
FIG. 21 is a cross-sectional view of the probe device of FIG. 14B taken along the line VI-VI'.

The coupling hook 737 is integrated with a rear surface of the lower housing 710 while rotating about a shaft 7374 of a side surface of the upper body 731, as illustrated in FIGS. 20 and 21. The coupling to the coupling hook 737 will be described later.

A probe pin guide 738 extending in the recessed portion 735 of the upper housing 730 and protruding upward is formed.

The probe pin guide 738 includes a hole 739 having a step so that a probe pin module 750 can be inserted, and the probe pin guide 738 guides the probe pin(s) 756 to connect the probe pin module 750 to the lower sensor pad 511 and the circuit board pad 158.

The probe pin guide 738 is formed with a stepped sidewall so that the support part 751 can be seated when the probe pin module 750 is inserted, the inside of the side wall is opened with a hole 739 through which the probe pin(s) 756 passes.

A connection hole for connecting the upper housing 730 and the upper cover 740 is formed next to the sidewall.

The connection hole is formed on steps on both sides of the hole 739 of the stepped sidewall.

Meanwhile, the upper body portion 731 includes a coupling hole 734 on the upper surface through which the coupling protrusion 714 of the lower housing 710 passes. The coupling hole 734 is aligned with the coupling hole 734 of the middle body 721, so that one coupling protrusion 714 is coupled to the coupling hole 734 of the middle body 721 and the coupling hole 734 of the upper body 731 while passing therethrough simultaneously.

The coupling hole 734 can be formed in three to correspond to the number and shape of the coupling protrusions 714. In this case, the two coupling holes 734 formed on the rear side can be formed along the sidewall of the recessed portion 735, that is, the stepped wall.

The probe pin module 750 is formed of a plurality of probe pins 756 supported by the support part 751, as shown in FIG. 15.

Each probe pin(s) 756 is positioned by the support 751. A plurality of fixing holes is formed in the support part 751, and each probe pin(s) 756 is fixed to the support part 751 through a corresponding fixing hole.

Each probe pin(s) 756 is formed in a bar type, and is formed as a conductive probe.

Each probe pin(s) 756 is formed to have a variable length according to a height of an object to be tested, and can be formed in a spring type, for example.

The plurality of probe pins 756 is formed such that one end (e.g., a first end) is exposed downward toward the object to be tested while the other end 755 (e.g., second end) are accommodated in the upper cover 740. The second ends of the probe pins 756 is illustrated in FIG. 15.

The plurality of probe pins 756 can be connected by wires so that the other ends 755 are electrically connected to each other according to a connection relationship of the object to be tested.

When the pad 511 to be tested is varied by variously deforming the respective fixing holes for the probe pins 756 of the support part 751 of the probe pin module 750, it is possible to use other components without deformation thereof only by deforming the probe pin module 750.

Meanwhile, the upper cover 740 is disposed on the upper surface of the upper housing 730.

The upper cover 740 covers the probe pin module 750 and has a structure for protecting the probe pin module 750 from the outside. The upper cover 740 includes a cover guide 748 for covering the probe pin guide 738, and an accommodating portion 745 extending from a lower portion of the cover guide 748 and covering the upper recessed portion 735 of the upper housing 730.

The cover guide 748 is placed on the probe pin guide 738, and is formed with a hole to receive the other ends 755 which is an upper portion of the probe pin(s) 756.

The cover guide 748 includes a coupling hole 749 passing through the coupling hole of the probe pin guide 738, and since the coupling holes 749 of the two structures are aligned, the coupling holes 749 can be simultaneously fixed by one connection member 760, that is, a screw member.

A front surface of the cover guide 748 is formed to have a predetermined height, and forms a front surface part of the probe device 700. In addition, an accommodating portion 745 is formed below the front surface of the cover guide 748 to cover the recessed portion 715 of the upper housing 730.

Accordingly, the front surface of the cover guide 748 can constitute a part of the sidewall of the accommodating portion 745.

The accommodating portion 745 is implemented in a concave shape in which a predetermined specimen can be accommodated, and an opening 746 for exposing the sensor area 540 of the sensor chip 500 is formed in a bottom of the accommodating portion 745.

As described above, by combining the plurality of modules in a state where the sensor chip 500 to be tested and the circuit board 150 are arranged, one probe device 700 is formed.

As described above, the lower housing 710 and the middle housing 720 can be coupled using a plurality of bonding materials. For example, as shown in FIG. 15, a screw hole 713, 723 is formed in each corner, one screw hole 713 of the lower housing 710 and one screw hole 723 of the middle housing 720 overlap each other to form a common screw hole 713, 723, and a single screw member is coupled to the screw hole 713, 723 to simultaneously couple the lower housing 710 and the middle housing 720. Alternatively, the lower housing 710 and the middle housing 720 can be formed by being fitted and coupled.

In addition, as shown in FIG. 19, the fitting protrusion 714 of the lower housing 710 and the coupling hole 724, 734 of the middle housing 720 and the upper housing 730 are fitted and coupled. In this case, a diameter of the coupling hole 734 can be formed such that a predetermined separation distance d5 is formed between the coupling protrusion 714 and the coupling hole 724, 734.

This is for tolerance, and the predetermined separation distance d5 can be formed to be 0.05 to 0.2 mm.

In addition to this protrusion coupling, the coupling hook 737 is disposed on both sides of the upper housing 730 for coupling with the middle housing 720 and the lower housing 710 from the upper housing 730.

FIG. 20 is an exploded cross-sectional view of the probe device 700 of FIG. 14B taken along line VI-VI', and FIG. 21 is a combined cross-sectional view of the probe device 700 of FIG. 14B taken along line VI-VI'.

Referring to FIGS. 20 and 21, the coupling hook 737 is rotatably coupled to the shaft 7374 from the side of the upper body 731 of the upper housing 730, and can cover and fix the side surface of the body portion of the lower housing 710 by rotation with respect to the shaft 7374.

As shown in FIG. 20, the coupling hook 737 includes a hook body 7373 coupled to the shaft and extending in an x-y side toward the upper body portion 731, and a hook handle 7371 extending upward and downward from the hook body 7373 and receiving a force to rotate the coupling hook 737 by the shaft 7374.

A lower portion of the hook handle 7371 includes a hook protrusion 7372 protruding inward from an end.

When a force is applied to the hook handle 7371, the lower portion of the hook handle 7371 spreads out as the hook body 7373 presses a lower spring member while rotating about the shaft. In this state, when the assembly of the middle housing 720 and the lower housing 710 is aligned with the lower portion of the upper housing 730 as shown in FIG. 21, the hook protrusion 7372 can be caught by a lower surface of the assembly while returning to the original position by the spring member.

In this case, as shown in FIG. 21, since there is some difference in area between the body portion 711 of the housing 720 and the lower housing 710, the step 719 can be formed in an area caught by the coupling hook 737, and the hook protrusion 7372 is coupled to the step 719 to further enhance the coupling of each structure in addition to the coupling by the coupling protrusion 714 and the coupling hole 734.

Due to this coupling, the lower portion of the probe pin(s) 756 is disposed to be connected to the pad 511 area of the sensor chip 500 and the connection pad 158 area of the circuit board 150.

Figure 22:
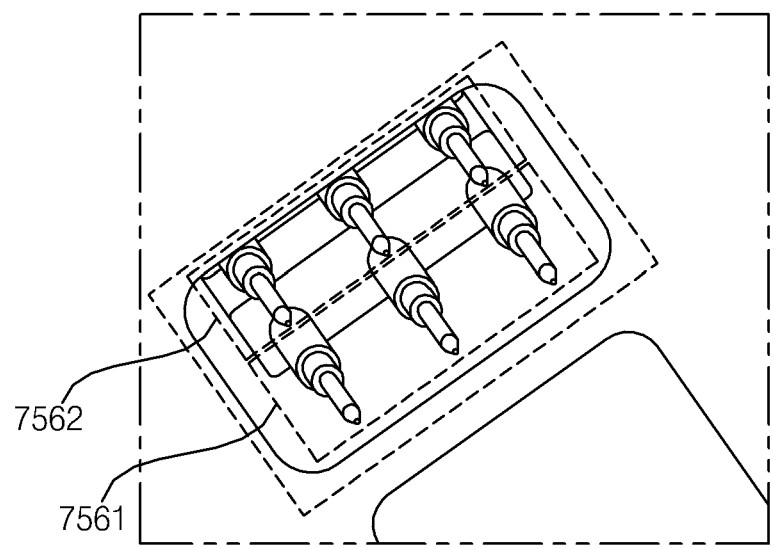
FIG. 22 is a view showing a shape of a probe pin exposed in a rear view of an upper housing.
Figure 23:
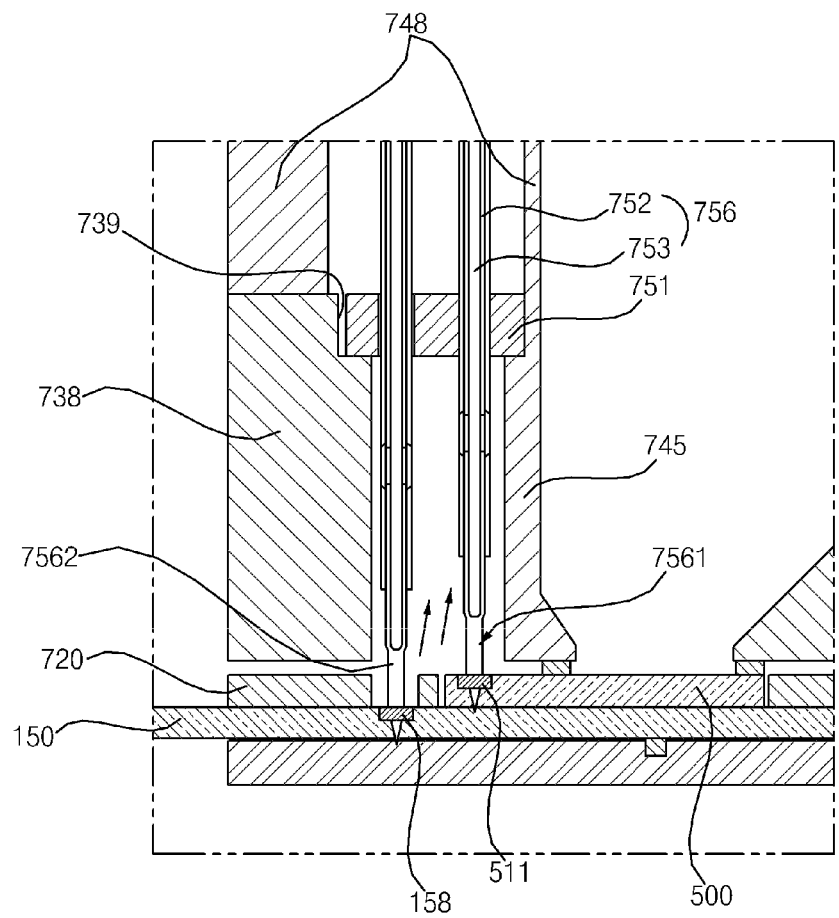
FIG. 23 is a cross-sectional view taken along line VII-VII' of the probe device of FIG. 14B.

FIG. 22 shows a shape of the probe pin(s) 756 exposed on a rear view of the upper cover 740, and FIG. 23 is a cross-sectional view of the probe device 700 of FIG. 14B taken along line VII-VII'.

For example, in FIG. 22, when the area of the pad 511 of the sensor chip 500 is formed of three pads 511 and the area of the connection pad 158 of the circuit board 150 is formed of three connection pads 158 corresponding thereto, three first probe pins 7561 arranged in a line in contact with the respective pads 511 of the pad 511 area of the sensor chip 500 and three second probe pins 7562 arranged in a line in contact with the respective pads 158 of the connection pad 158 area of the circuit board 150 are exposed.

The first probe pins 7561 and the second probe pins 7562 can be arranged in adjacent rows.

As shown in FIG. 23, the probe pin(s) 756, the pad 511 of the sensor chip 500 and the connection pad 158 of the circuit board 150 are bonded by assembling of the assemblies as described above.

In this case, when the probe pins 756 are formed of a variable length and each probe pin(s) 756 is formed, for example, in a bar type, the probe pins 756 are formed of double layers 752 and 753 so that the probe pins 756 are inserted so as to overlap by a predetermined distance according to a height of the connection pad 158 of the circuit board 150 to be tested and a height of the pad 511 of the sensor chip 500.

Therefore, even if there is a difference in height of a target specimen between the first probe pin(s) 756 and the second probe pin(s) 756, all the probe pins 756 can come into contact with the specimen by adjusting a length of each probe pin(s) 756.

A performance test of the sensor chip 500 is possible by applying one sample sensor chip 500 and the circuit board 150 by the probe device 700 as described above.

Specifically, as described with reference to FIG. 13, the circuit board 150 is seated in the accommodating portion 715 of the lower housing 710 so that a board coupling portion is coupled to a board coupling hole 734 (S141). In this case, the connection terminal 153 of the circuit board 150 is disposed to be exposed to the outside.

When the connection terminal 153 of the board is exposed to the outside, the connection terminal 153 can be disposed to be exposed rearwardly unlike as shown in FIG. 6. That is, the circuit board 150 can be disposed upside down so that the connection pad 158 for contact with the sensor chip 500 is placed on the front side.

Alternatively, when the connection pad 158 of the circuit board 150 is formed on both sides, the circuit board 150 can be placed on the front side.

Next, after the screw holes 713 and 723 of the lower housing 710 and the middle housing 720 are coupled to be fitted together, a screw member is fastened to the coupling hole 71 to form an assembly (S142).

The sensor chip 500 is seated on the exposed middle body portion 721 of the middle housing 720.

The sensor chip 500 can be a single diced sensor chip 500 or a sample sensor chip 500.

The sensor chip 500 is disposed in the chip area 725 of the recessed portion 715 so that the pad(s) 511 of the sensor chip 500 is/are disposed on the rear side of the chip area 724. In this case, the sensor chip 500 can be disposed on the chip area 725 using a tweezer or the like, and since all corner areas are chamfered, the sensor chip 500 can be disposed without damage.

Next, after the probe pin module 750 is mounted on the probe pin guide 738 of the upper housing 730, the upper housing 730 and the upper cover 740 are coupled (S143).

The upper housing 730 and the upper cover 740 can be formed by fastening a screw member to the connection hole 749 formed in the probe cover 748 of the upper cover 740.

When the upper housing 730 and the upper cover 740 are coupled, the probe module 750 is formed to expose a lower portion of the probe pin(s) 756 on the rear surface of the upper housing 730 as shown in FIG. 22.

The assembly of the upper housing 730 and the upper cover 740 is assembled with the assembly of the lower housing 710 and the middle housing 720 to complete the coupling of the probe device 700.

In the coupling between the assemblies, while the coupling protrusion 714 and the coupling hole 734 are coupled to be fitted, a force is applied to the upper portion of the hook handle 7371 of the coupling hook 737 of the upper housing 730 so that the lower portion of the hook handle 7371 is opened to the outside, and while the lower portion of the hook handle 7371 returns back to its original position, the hook protrusion 7372 is caught on the rear surface or the step of the middle housing 720.

As described above, the assemblies can be more stably coupled through the double fastening, and the two assemblies can be separated by applying a force again since there is no thermochemical structural change.

As described above, when the coupling of the probe device 700 is completed as the sensor chip 500 to be tested and the circuit board 150 are coupled, the probe device 700 can function as an intermediary unit and can perform a test through the exposed connection terminal 153 of the circuit board 150 (S144).

That is, in a state in which a reference solution, for example, an electrolyte solution such as water, is injected into the accommodating portion 745 of the probe device 700 to connect the gate electrode and the channel of the sensor chip 500 to the probe device 700, a test is performed by inserting the probe device 700 into test equipment.

The test can be performed, for example, by measuring a reference resistance of the sensor chip 500. To this end, a gate voltage and a source voltage are transferred to the connection pad 158 of the circuit board 150 through the connection terminal 153 and transferred to the first probe pin(s) 756 through the second probe pin(s) 756, and transferred to the pad 511 of the sensor chip 500 by the first probe pin(s) 756.

Therefore, when the gate voltage and the source voltage of the sensor chip 500 are set and a drain current of the sensor chip 500 is read accordingly, the reference resistance value of the sensor chip 500 can be calculated according to the drain current.

In this case, if the drain current is not read or is very high, it can be determined that there is an error in the sensor chip 500.

As such, when the drain current is read and falls within a predetermined range, the reference resistance value can be calculated based on the value of the drain current and an operating range of the sensor chip 500 can be determined accordingly.

When it is determined that the sample sensor chip 500 operates normally, a process is performed to disassemble coupled members into respective housings, collect the sensor chip 500 and the circuit board 150, and couple the circuit board 150 and the sensor chip 500 with the biosensor cartridge 100 (S145).

Figure 24:
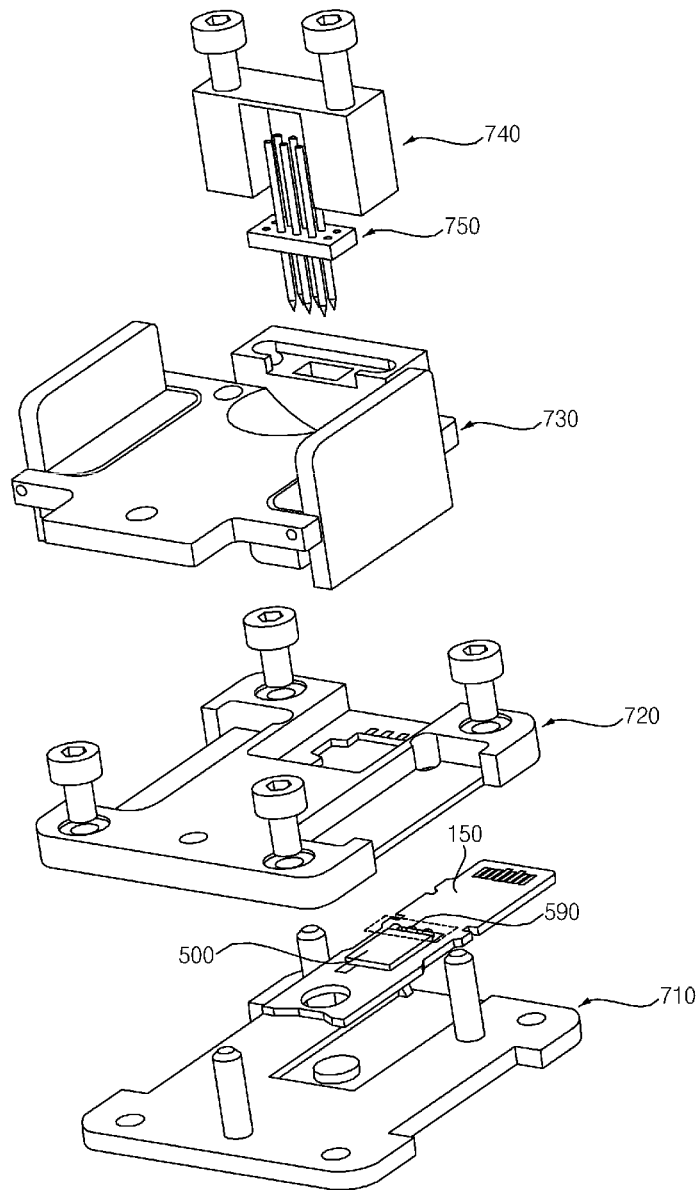
FIG. 24 is an exploded perspective view illustrating another example of the probe device of FIGS. 14A and 14B.

FIG. 24 is an exploded perspective view illustrating another example of the probe device 700 of FIGS. 14A and 14B.

The probe device 700 of FIG. 24 has the same configuration as one example of the probe device 700 of FIGS. 14A to 23, except for a configuration of an object to be tested.

That is, referring to FIG. 24, the circuit board 150 and the sensor chip 590 are disposed in an electrically conductive state.

That is, the connection pad 158 of the circuit board 150 and the pad 511 of the sensor chip 590 are placed in the lower housing 710 in a state in which the connection pad 158 and the pad 511 are electrically connected through wire bonding or a connection clip.

Therefore, the sensor chip 590 bonded to the circuit board 150 is exposed to the chip opening of the middle housing 720.

This line coupling can prevent a test error due to misalignment of the circuit board 150 and the sensor chip 590.

In this case, the upper cover 740 can be implemented as the same as the upper cover 740 described above, but can be configured only with the cover guide 748 without the accommodating portion 745 as shown in FIG. 24. As such, when only the cover guide 748 is formed, the recessed portion 715 of the upper housing 730 can function as the accommodating portion 745.

Various embodiments described herein may be implemented in a computer-readable medium using, for example, software, hardware, or some combination thereof. For example, the embodiments described herein may be implemented within one or more of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, other electronic units designed to perform the functions described herein, or a selective combination thereof. In some cases, such embodiments are implemented by the controller. For Example, the controller is a hardware-embedded processor executing the appropriate algorithms (e.g., flowcharts) for performing the described functions and thus has sufficient structure. Also, the embodiments such as procedures and functions may be implemented together with separate software modules each of which performs at least one of functions and operations. The software codes can be implemented with a software application written in any suitable programming language. Also, the software codes can be stored in the memory and executed by the controller, thus making the controller a type of special purpose controller specifically configured to carry out the described functions and algorithms. Thus, the components shown in the drawings have sufficient structure to implement the appropriate algorithms for performing the described functions.

For a software implementation, the embodiments such as procedures and functions may be implemented together with separate software modules each of which performs at least one of functions and operations. The software codes can be implemented with a software application written in any suitable programming language. Also, the software codes may be stored in the memory and executed by the controller. Thus, the components shown in the drawings have sufficient structure to implement the appropriate algorithms for performing the described functions.

The present invention encompasses various modifications to each of the examples and embodiments discussed herein. According to the invention, one or more features described above in one embodiment or example can be equally applied to another embodiment or example described above. The features of one or more embodiments or examples described above can be combined into each of the embodiments or examples described above. Any full or partial combination of one or more embodiment or examples of the invention is also part of the invention.

The present invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A probe device for testing a sensor chip that detects a target material from an applied analysis specimen, has a reactant reacting specifically with the target material, and transmits a generated electrical signal, the probe device comprising:
a lower housing configured to accommodate a circuit board of the sensor chip, the circuit board including a connection terminal configured to be electrically connected to an external test device;
a middle housing coupled to the lower housing, the middle housing configured to have the sensor chip mounted thereon;
a probe module including a plurality of probe pins for connecting a pad of the sensor chip to a connection pad of the circuit board; and
an upper housing coupled to the middle housing, the upper housing including a guide area having a recessed portion that exposes a sensor area of the sensor chip,
wherein the middle housing includes a plurality of pin openings which exposes the connection pad of the circuit board, and
wherein some of the plurality of probe pins passes through the plurality of pin openings.

2. The probe device claim 1, wherein the upper housing aligns the probe module on the pad of the sensor chip and on the connection pad of the circuit board.

3. The probe device of claim 2, wherein the middle housing includes a chip area configured to accommodate the sensor chip so that the pad of the sensor chip is disposed adjacent to the plurality of pin openings.

4. The probe device of claim 3, wherein the probe module further includes a support part for supporting the plurality of probe pins, and
wherein the plurality of probe pins are configured to pass through the support part and contact the pad of the sensor chip and the connection pad of the circuit board.

5. The probe device of claim 4, wherein a length of each of the plurality of probe pins is adjustable according to a height of the sensor chip and a height of the circuit board.

6. The probe device of claim 5, wherein the support part has a plurality of fixing holes,
wherein the plurality of probe pins pass through the plurality of fixing holes of the support part, and
wherein the plurality of probe pins are insulated from each other by the support part.

7. The probe device of claim 4, wherein a first end of each of the plurality of probe pins is exposed above the support part,
   wherein a second end of each of the plurality of probe pins is exposed below the support part, and
   wherein an electrical connection between the pad of the sensor chip and the connection pad of the circuit board is made by second ends of the plurality of probe pins.

8. The probe device of claim 4, wherein the recessed portion of the guide area is inclined to accommodate the upper housing an electrolyte fluid.

9. The probe device of claim 8, wherein the guide area of the upper housing further comprises a probe pin guide for supporting the support part of a probe pin module.

10. The probe device of claim 9, wherein the upper housing includes a body portion, and
    wherein the probe pin guide protrudes from the body portion of the upper housing by a predetermined height.

11. The probe device of claim 10, further comprising:
    a cover guide disposed on the probe pin guide and housing one end of the plurality of probe pins.

12. The probe device claim 1, wherein the lower housing includes:
    a body portion in contact with the middle housing, and
    at least one coupling protrusion protruding from an upper surface of the body portion.

13. The probe device of claim 12, wherein the at least one coupling protrusion passes through the middle housing, and
    wherein the at least one coupling protrusion is coupled to the upper housing.

14. The probe device claim 1, wherein the lower housing includes coupling holes,
    wherein the middle housing includes coupling holes overlapping the coupling holes of the lower housing, and
    wherein the lower housing is fixed to the middle housing by fasteners extending through the coupling holes of the lower housing and through coupling holes of the middle housing.

15. The probe device claim 1, wherein the upper housing includes a coupling hook engaged with the lower housing or the middle housing.

16. The probe device claim 1, wherein the probe module is configured to measure a reference resistance of the sensor chip by inserting the connection terminal of the circuit board into the external test device with an electrolyte fluid applied to the recessed portion.

17. A probe device for testing a sensor chip that detects a target material from an applied analysis specimen, has a reactant reacting specifically with the target material, and transmits a generated electrical signal through a pad, the probe device comprising:
    a lower housing configured to accommodate a circuit board;
    a middle housing coupled to the lower housing and having a recessed part, the middle housing configured to have the sensor chip mounted thereon;
    a probe module including a plurality of probe pins electrically connected to each other for connecting a pad of the sensor chip to a connection pad of the circuit board; and
    an upper housing including a coupling hook, the upper housing being coupled to the recessed part of the middle housing and the lower housing by the coupling hook,
    wherein the middle housing includes a plurality of pin openings which exposes the connection pad of the circuit board, and
    wherein some of the plurality of probe pins passes through the plurality of pin openings.

18. The probe device of claim 17, wherein the upper housing further includes a shaft rotatably connected to the coupling hook, and
    wherein rotation of the shaft causes the coupling hook to be coupled to or decoupled from the recessed part of the middle housing.

19. The probe device of claim 17, wherein the middle housing includes the plurality of pin openings exposing the connection pad of the circuit board, and
    wherein the upper housing includes a probe pin guide supporting a probe pin module.

20. The probe device of claim 19, further comprising a support part including a plurality of openings for supporting the plurality of probe pins,
    wherein the probe pin guide of the upper hosing includes a stepped sidewall, and
    wherein the support part is disposed on the stepped sidewall of the probe pin guide of the upper housing.

* * * * *